United States Patent
Smith

(10) Patent No.: US 6,617,123 B1
(45) Date of Patent: Sep. 9, 2003

(54) METHOD FOR DETECTION OF 4-HYDROXYBUTYRIC ACID AND ITS PRECURSOR(S) IN FLUIDS

(76) Inventor: Jack V. Smith, 44 WoodsEdge Dr., Asheville, NC (US) 28732

( * ) Notice: Subject to any disclaimer, the term of this patent is extended or adjusted under 35 U.S.C. 154(b) by 0 days.

(21) Appl. No.: 09/607,026

(22) Filed: Jun. 29, 2000

(51) Int. Cl.[7] .................................................. C12Q 1/44
(52) U.S. Cl. ............................. 435/19; 435/7.9; 435/26
(58) Field of Search ............................. 435/26, 19, 7.9

(56) References Cited

U.S. PATENT DOCUMENTS

| | | | |
|---|---|---|---|
| 4,351,899 A | * | 9/1982 | Owen |
| 4,622,296 A | * | 11/1986 | Yaminishi et al. |
| 5,032,506 A | * | 7/1991 | Palmer et al. |
| 5,624,813 A | * | 4/1997 | Mahant |
| 5,912,139 A | * | 6/1999 | Iwata et al. |

FOREIGN PATENT DOCUMENTS

EP   0291194 A1  * 11/1988

OTHER PUBLICATIONS

Derwent abstract of JP 60066993A (Acc. No. 1985–130835). Measuring components in body fluid–using oxidoreductase, electron carrier and color developer after removal of interfering substances, Apr. 1985.*

EP 0226427 A2. Asai et al. (1987). Method for simultaneously carrying out quality inspection of animal milk and health inspection of the animal, and indicator therefor.*

* cited by examiner

*Primary Examiner*—Ralph Gitomer

(57) ABSTRACT

A method for determining the presence or amount of gamma-hydroxybutyrate or precursors in a sample, said method comprising contacting said sample with an indicator which specifically binds to gamma-hydroxybutyrate or precursors to form an indicatorcomplex; and, measuring said indicatorcomplex to determine the presence or amount of said gamma-hydroxybutyrate or precursors in said sample.

7 Claims, No Drawings

METHOD FOR DETECTION OF 4-HYDROXYBUTYRIC ACID AND ITS PRECURSOR(S) IN FLUIDS

BACKGROUND OF THE INVENTION

1. Field of the Invention

As the use of illicit drugs in this country has increased, public concern over the problems associated with its effects has grown into a major concern. This concern has led to workplace drug testing in order to identify, treat, and remove active drug users from the workforce. This trend started in the military, and spread rapidly to law enforcement and any "safety-sensitive" private sector jobs such as airline pilots, truck drivers, and active crew members of public transportation. These initial strides into drug testing in the workplace revealed the obtrusive incursion of drug use and abuse in the daily lives of a significant portion of Americans. Further research indicated the staggering costs to public and private industry in terms of lost productivity, increased health care costs, and human suffering and death due to this scourge of drug abuse. As a result, drug testing has rapidly spread to all areas of the public and private sector. The vast majority of workplace drug testing has taken the form of urine testing, because of ease of collection, low cost, and effective indication of recent drug use. Other forms of testing include analysis of blood, saliva, sweat, and hair.

Gamma-hydroxybutyrate (4-hydroxybutyrate, 4-hydroxybutyric acid, Gamma-hydroxybutyric acid, 4-hydroxybutyric acid sodium salt, GHB) was first used for anesthetic purposes in 1961, because it was unpredictable and caused adverse effects, its use was discontinued. Later, GHB was used by body builders for muscle building and weight control. Presently, the U.S. DEA (Drug Enforcement Agency) is investigating GHB to see if it should be a controlled substance. The U.S. FDA (Food and Drug Administration) list GHB as an unapproved drug except for investigational use in the treatment of narcolepsy. Common names for GHB are Scoop, Georgia Home Boy, Grievous Bodily Harm, Liquid Ecstasy, and Cherry Meth among others. Its precursor GBL (gamma-butyrolactone) is used as a GHB substitute and once ingested rapidly converts to GHB. The pharmacological effects of both GHB and GBL are similar and the range of analgesic effect (euphoria) are similar.

In the 1990's GHB has become a popular drug of abuse on college campuses, bars, and dance clubs and is called the "date rape" drug. The abuse of GHB has enormous sociological and economic impact on our society. A typical "date rape" scenario is as follows: The victim(s), usually women, are in a bar, they drink a beverage that has been laced with GHB by a rapist, the victim then becomes catatonic and is usually agreeable with anyone and everyone around them. They can become unconscious and then of course are susceptible to the rapist desires. Later, the victim(s) wakes up completely disoriented, naked and robbed. This type of horrific tragedy is occurring on a daily basis. The victims of "date rape" are not only exposed to the physical assault of rape and robbery, but to the contraction of diseases such as AIDS and STD's. The damage caused and the consequences of such occurrences are immeasurable.

Accordingly, a need exists for providing an easy and convenient manner by which to make a determination of the presence of GHB in urine, in a beverage, or other biological fluids or liquids. A further need exists for a convenient manner by which such determinations may be made by using rapid analysis manual techniques (such as a dipstick or lateral flow devices) and automated techniques that will advance the art significantly. And, the most important need is for a device that would detect GHB using just a single assay that does not require an extraction process or lactone conversion. This would be a marked advancement in the art and would result in the savings of millions of dollars to the drug testing laboratories required to perform GC (gas chromatography) or GCMS (gas chromatography mass spectrometry) testing for GHB and obviously this savings would be passed on to the end user (the businesses which initially request drug's of abuse assays on perspective and current employees). To explain further, the drug testing laboratory would normally perform GC (gas chromatography) or GCMS (gas chromatography mass spectrometry) assay for GHB. The necessary time to perform these assays is burdensome to the laboratory through cost for tech time, reagents, and turnaround time to mention a few. The alternative to this would be the significant advancement in the art that the present device offers which is the capability to detect GHB without lengthy extraction processes of the current art with a single assay.

2. Description of the Related Art

This invention is in the field of toxicology. More specifically, this invention provides test strips (i.e. dry chemistry dipsticks, or on-site test modules utilizing thin layer chromatography in a lateral flow format, or other similar technology to the test strip) and liquid chemistry reagents for use in the detection of GHB with a single assay in aqueous fluids to include but not limited to urine, saliva, serum, blood, sweat extracts, liquid homogenates of hair and liquids such as beverages, soft drinks, mixed drinks to included alcohol, etc.

It is known that the polarity and small molecular size of the GHB molecule and the lack of detectability of the GHB by UV (ultra violet), chromatographic, and spectrophotometric means complicates detection. GHB is relatively unstable and will form the GHB lactone derivative when heated and under acidic conditions. GHB can cause euphoria at less than 50 ug/mL to marked central depression, sleep, coma and death. Currently, all of the methods to detect GHB use and/or solid-phase extraction, liquid-liquid extraction, silyl-derivatization, then GCMS. These methods mentioned are very time consuming, expensive (costing the laboratories, companies ordering drug testing, and general public millions of dollars per year), and labor intensive. The GC-MS, assay is typically performed to verify the urines that screen positive for drugs of abuse. The GC-MS analysis costs 100 times as much as the initial screen ($100 vs $1). Every additional unnecessary GC-MS performed drives up the overall cost of drug testing.

The novel invention described herein describes a method to determine the presence or absence of GHB and its precursor(s) in urine or other fluids by liquid and dry chemistry test means which has not been taught prior to the present art. It should be noted that GHB is not normally found in urine.

There are no published, taught, or even mentioned methods of the present arts technology to detect GHB or GBL in urine by the present arts techniques.

Again, a thorough search of patents and research revealed no relative art (i.e., prior art) with any correlation to this technology. The art of testing for GHB or GBL in urine or other fluids as previously delineated in the literature describe various techniques including methods for solid-phase extraction, liquid-liquid extraction, silyl-derivatization, then GCMS. No reference, however, has described this new art as delineated here. The previous art will be enumerated here to further illustrate the unique advancement in the field of GHB and GBL detection. It has been acknowledged in the art that random urinary sample matrices are very complex, and consist of many urinary constituents which create strong buffering and interference problems (e.g. cannibal like enzymes such as protease). In addition, disease states will significantly impact the nature of urinary contents. Urine is also the repository of all of the body's waste products including excess parent nutrients, vitamins, drugs, and their metabolites. These waste chemicals vary from person to person and significantly contribute to the individual uniqueness that makes assay design for urinary constituents more difficult than any other body fluid. All of these factors impact an assay's ability to obtain acceptable precision and accuracy. The ability of an assay to analyze a biological liquid such as saliva, therefore, rarely ever translates to an effective assay for urine. Therefore the present invention's ability to effectively cope with random urine samples and biological fluids or other fluids such as a beverage(s) makes it unique.

Patent, U.S. Pat. No. 3,603,957, discloses the use of assay test strips, but fails to teach a method for the determination of GHB or GBL of a test sample submitted for drugs of abuse testing. It also doesn't teach a method to determine the presence or absence of any substance such as GHB or GBL. The patent doesn't teach the use of the present art's reaction formula to dry chemistry format called a dipstick or lateral flow technology that not only is completely novel, but prevents cross contamination between test pads typically found on a test strip (dipstick). In addition, this patent also failed to mention any methods for determination of GHB or GBL by dipstick, lateral flow, calorimetric, liquid reagent (automated) or other suitable means.

Another patent, U.S. Pat. No. 4,301,115, discloses the use of assay test strips, and the ability of the assay strips to resist cross contamination between reactant areas (chemically impregnated test pads), but fails to teach a method for the determination of GHB or GBL in a sample of fluid. The patent doesn't teach the use of the dry chemistry format utilizing either a dipstick or lateral flow device, liquid reagent (automated) method or mention any methods for determination of GHB or GBL.

Another patent, U.S. Pat. No. 5,447,837, does mention the use of assay test strips but again fails to disclose a method for the determination of GHB or GBL. This is a method for detection of an antigenic substance in human, biological samples. This patent also fails to mention the use of a reaction formula that is adaptable to the dry chemistry format utilizing either a dipstick or lateral flow device. It also doesn't teach a method to determine the presence or absence of any substance such as GHB or GBL. In addition, this patent also failed to mention any methods for determination of GHB or GBL by dry chemistry, liquid chemistry, calorimetric, or other suitable means.

Published literature and the prior art describes techniques such as ELISA that have been used to determine the presence of drugs of abuse, but these technologies have no relevant bearing on the present device. Previously taught technologies include measurement of GHB or GBL using GC or GCMS techniques and the required extraction procedures inherent (required) prior to analysis by GC or GCMS.

Therefore, in a nutshell, the present device provides an absolute novel approach to GHB or GBL testing and lateral flow testing using dry chemistry test pads and automated liquid reagent testing.

Not surprisingly, it is known and is illustrated here that a great need exists in the field of drug testing for rapid, economical, and effective method for the detection of GHB or GBL on samples submitted for testing, whether liquid chemistry and/or dry chemistry methodology using dipsticks or lateral flow test devices (for single use and for on-site collections). The present invention does detect GHB or GBL effectively with a single assay and therefore and accordingly, the present device provides an easy and convenient manner by which to make a determination of the presence or absence of GHB or GBL in a fluid. The present art's use of lateral flow also enables the removal of any interference of any cross over of reagents or fluid from one test pad to another which is one of the exclusive problems with dipsticks.

It is clear that a need exists for a convenient manner by which a determination of GHB or GBL can be made utilizing a rapid automated analysis utilizing a liquid reagent format of the present device or manual analysis in the form of dry chemistry (dipstick) and/or lateral flow test devices. These and other advances in the current state of the art will become evident in view of the present specification and claims.

SUMMARY OF THE INVENTION

Briefly stated, the present invention relates to the test devices for detecting the presence of GHB and or its precursor GBL (gamma-butyrolactone) in a liquid test sample and the methods for making said devices. GBL is also used as a GHB substitute. Once ingested, GHL is rapidly converted to GHB. GHB can also be converted to GBL by acid catalysis. This invention is in the field of drug testing. More specifically, this invention provides dry chemistry test strips (i.e. dipsticks, or dry chemistry and lateral flow [thin layer chromatography] test means) or automated or manual liquid reagent means for use in the detection of GHB or GBL in biological samples (e.g. urine, blood, serum, saliva, sweat extracts, and hair homogenates) or other fluids such as beverages, water, soft drinks, alcoholic drinks to name a few. This invention achieves this goal by measuring the presence of GHB or GBL in a test sample. And, this invention provides a unique method for preventing cross contamination between test pads (reactant areas) on dipsticks by the present inventions use of the dipstick test pad and lateral flow device technology. This invention provides a previously unavailable dry chemistry or liquid chemistry method for determining GHB or GBL presence in a test sample by measuring the presence of GHB or GBL.

The present invention encompasses a method that can utilize several different techniques. The techniques would employ the manual method using dry chemistry dipsticks and the method of combining dry chemistry dipstick reactant areas (test pads) with lateral flow thin layer chromatography or the method of using a liquid reagent that is compatible with automated analyzers that provide high speed quantitative analysis which would be much less labor intensive than the manual methods providing a savings in time and money. The widespread utility of the present art also provides the drug testing laboratory, over-the-counter user, individual, police agency, drug testing collection site (where the urine is actually collected), or other users the choice of using the dry chemistry (manual) or automated liquid means which ever method best suits their situation or needs.

The present arts technique utilizes two dry chemistry techniques, one is dipsticks, which is a carrier dependent, rapid test that uses absorbent medium such as paper which have been impregnated with a chemical formulation to detect adulteration. After dipping one (dipstick) into a liquid test sample, a reaction takes place. Said resulting reaction will yield a color change indicating a positive or negative result (i.e. presence or absence of GHB or GBL). The other technique is the use of lateral flow in combination with a dry chemical test pad. The lateral flow device is a rapid test that uses absorbent medium such as paper which has been impregnated with the chemical formulation to detect GHB or GBL. The paper, after impregnation, is then placed on a lateral flow medium, such as nitrocellulose paper, glass fiber paper, or other suitable wicking material that will deliver the test sample to the impregnated paper. The lateral flow device works by dipping one end of the lateral flow device (LFD) into a sample (urine for example). The urine migrates up (along) the paper (or absorbent material) to the reactive sites (test paper) containing reagents (reactive ingredients). The urine constituents react with the assay reagents during the migration process and yield visible results. The urine can also be droppered onto the LFD and the sample will then migrate along the paper.

The ease of use and rapid results obtained by the present art's methodology illustrate the unique utility of this testing technique. In addition, very little technical expertise is required to perform this type of assay (no instrumentation required). Furthermore, the early detection of GHB or GBL facilitates the prevention of the "date rape" syndrome. This novel concept for GHB or GBL monitoring provides an enormous savings of time and money. The present arts method(s) of GHB or GBL testing utilizing these techniques are currently not available and have never been taught.

An important aspect of GHB or GBL testing in fluids is the sensitivity of the test method. Both techniques taught here have an effective sensitivity range comparable to the GC-MS target range. The sensitivity can also be adjusted to indicate a large amount present as would be the case if the sample tested were a soft drink spiked with GHB or GBL. Obviously, the amount in a sample directly spiked with GHB or GBL would be much higher in concentration than the amounts found in urine. The dipstick test and LFD dipstick hybrid (to be known as the LFD hybrid) have a quantitative to qualitative assay range. The results are evaluated via one of following categories: negative, positive, or quantitatively.

The present arts technique also utilizes a liquid chemistry test means that allows for rapid analysis via an automated analyzer that can yield high speed quantitative results. This will result in rapid test results, improved accuracy, lowered labor cost, and better turn around on a high volume of test. This automated method is only limited by the speed of the automated analyzer. Some analyzers currently on the market are capable of over 10,000 test per a hour. The ability of the present art to perform a single assay on a high speed automated analyzer that is capable of detecting GHB or GBL has never been present or taught in the prior art.

It is currently known in the art that enzyme and antigen/antibody reaction kinetics are related to the rate of change in analytical, biological systems. The variables that affect this rate of change include concentration of reactants and product, temperature, pH, ionic strength, buffer strength, and other parameters. The present art's innate and unique ability enables it to determine the presence of GHB or GBL in fluids. As it is known in the art urine is a very complex matrix and the measurement of GHB or GBL in fluids such as urine has to take into account many factors which will affect the assay.

The composition of the formulation to be applied to the dry chemistry dipstick, LFD hybrid and liquid chemistry method are composed of indicator(s) (visible calorimetric), and buffer(s).

Briefly stated, the present invention relates to test devices for measurement of GHB or GBL in urine but could also work in other biological matrices such as blood, saliva, hair or other fluids and the procedures for making said test means. This invention is in the field of clinical diagnostics. More specifically, this invention provides dry chemistry dipsticks (DCD's or on-site test modules), thin layer lateral flow chromatographic dry chemistry technology (LFD's), and the combination of both in a unique hybrid that is not known prior to the present art and liquid chemistry reagents for automated and manual use. That is to say (in it's simplest terms) that this unique hybrid (LFD) will encompass the use of a dry chemistry test pad resting on the surface of a wicking material (such as nitrocellulose) acting as a fluid delivery device. This new art can utilize aqueous, biological specimens including urine, saliva, sweat extracts, blood, serum and other fluids (such as water or soft drinks, etc.). Thus, this invention provides a unique method for GHB or GBL measurement utilizing rapid test devices including the automated method as well as the DCD, and LFD methodology thereby enabling in-home, workplace, and recreational testing through over-the-counter (OTC) sales. This is an enormous advancement in the art. These advances and improvements of the present device over the prior art provides the public safety, health care and drug testing industry with powerful new clinical and diagnostic tools.

A thorough search of the literature reveals no relative art resembling this technology; therefore, this invention is clearly a novel creation, and is not obvious to anyone skilled in the art of toxicology and clinical chemistry.

DETAILED DESCRIPTION OF THE INVENTION

The instant invention is a single assay in the form of a liquid chemistry reagent, dry chemistry dipstick or lateral flow device in conjunction with using a dry chemistry test pad for the detection of GHB or GBL in sample matrices consisting of urine and other biological specimens (e.g. saliva, serum, blood, sweat extracts, and hair homogenates) or fluids such as beverages such water, soft drinks, beer, or mixed drinks. The GHB or GBL detection assay that makes up the instant invention may take the form of dry chemistry dipsticks or dry chemistry test pad lateral flow hybrid, both of which are composed of some or all of the following compounds: buffer(s) and color indicator(s), hereinafter referred to as the adulteration reagent or the liquid automated reagent designed for high speed automated analyzers also composed of some or all of the following compounds: buffer(s) and color indicator(s). It can be noted that the liquid reagent method could also be used manually employing spectrophotometers or other types of visual detection technology. Buffering of the reactants is critical to the GHB or GBL reagent, because pH plays a vital role in the reaction kinetics. In the case of the dipstick (or dry chemistry dipstick, DCD) and the dipstick/lateral flow hybrid (which can be known as the "DLFH" device), GHB or GBL reagent components are impregnated on the test strip pad composed of solid, absorbent carrier(s), usually known as test pads. In the case of dipsticks, these test pads are typically affixed to a solid support (usually plastic). This device is then submerged in the liquid test sample, removed, and a measurable (i.e. visible) response is observed. Or in the case of the DLFH, the dry chemistry test pad is chemically impregnated identically to the dipstick. The test pad is then placed in fluid (direct) contact with lateral flow paper (such as nitrocellulose). This device is then exposed to a fluid (urine for example). The urine then migrates to the location of the test pad, saturates the test pad, and the reaction takes place.

The GHB or GBL reagents of the device constitute the heart of the analytical response provided by it, and is comprised of one or more reagent compositions responsive to any number of chemical components made up of GHB or GBL or are analogs or precursors of GHB. The reagents, in the broadest sense produces a detectable manifestation of the presence of GHB or GBL; the detectable manifestation can be a measurable response in the form of the appearance or disappearance of a color, or the changing of one color to another. Said measurable response may also be evidenced by a change in the amount of light reflected or absorbed during the reaction of interest. The analytical arts are replete with examples of these types of detectable responses.

In the present invention, there is provided a dry chemistry test strip in the form of a dipstick or DLFH for the detection of GHB or GBL in urine (or other biological fluids including saliva, sweat extracts, serum, blood, and hair homogenates) and fluids such as beverages to included but not limited to water, soft drinks, beer, or mixed drinks (possibly containing alcohol) comprising a solid, carrier matrix in the form of a dry chemistry dipstick containing an indicator compound and buffer.

The present technology does not predict or forecast the obvious advancement in the art to encompass the present invention, nor does it hint at the extraordinary improvement the present invention provides in the field of GHB or GBL detection. While urine is the sample matrix of choice for this instant invention (and for the immunoassays currently in general use for drug abuse screening) it is well within the scope of this novel invention to utilize it in the analysis of other sample matrices including saliva, sweat extracts, serum, hair homogenates, gastric contents, cerebral spinal fluid, blood and fluids such as beverages to included but not limited to water, soft drinks, beer, or mixed drinks (possibly containing alcohol).

The remarkable discovery of the new art formula will require the presence of an indicator(s) for GHB or GBL in urine (as well as the other matrices mentioned) that was unknown prior to this art. The newly discovered and suitable indicators and compounds that are reactive to the presence of GHB or GBL are but, not limited to the following; hydroxybutyrate dehydrogenase, esterase, 3-hydroxybutyrate dehydrogenase, 4-hydroxybutyrate dehydrogenase, carboxyl esterase, carboxylic-ester hydrolase, β-hydroxybutyrate dehydrogenase, [R]-3-hydroxybutanoate, NAD (nicotinamide adenine dinucleotide)$^+$ oxidoreductase, NAD (α-nicotinamide adenine dinucleotide) or analogs of NAD such as 3-acetylpyridine adenine dinucloetide, 3-acetylpyridine hypoxanthine dinucleotide, β-nicotinamide adenine dinucleotide-agarose, nicotinamide 1,N$^6$-ethenoadenine dinucleotide, nicotinamide guanine dinucleotide, nicotinamide hypoxanthine dinucleotide, nicotinic acid adenine dinucleotide, 3-pyridinealdehyde adenine dinucleotide, thionicotinamide adenine dinucleotide and α-hydroxybutyrate dehydrogenase, NADP (α-nicotinamide adenine dinucleotide phosphate) or analogs of NADP such as β-nicotinamide adenine dinucleotide phosphate, 3-acetylpyridine adenine phosphate, β-nicotinamide adenine dinucleotide 2',3'-Cyclic monophosphate, β-nicotinamide adenine dinucleotide 3'-phosphate, nicotinamide 1,N$^6$-etheno adenine dinucleotide phosphate, nicotinamide hypoxanthine dinucleotide phosphate, thionicotinamide adenine dinucleotide phosphate and anti-gamma-hydroxybutyrate, gamma-butyrolactone dehydrogenase, anti-gamma-butyrolactone, alpha-nicotinamide adenine dinucleotide phosphate, beta-nicotinamide adenine dinucle-otide phosphate and all analogs of the afore mentioned, and can be selected from the following group consisting of NBT (nitro blue tetrazolium), phenazine methosulfate, tetranitroblue tetrazolium, napthol AS-TR phosphate, methylene blue, Fast red, napthol-AS-MX, napthol AS-TR phosphate, thymol blue, bromcresol green, methyl red, cresol red, metanil yellow, m-cresol purple, xylenol blue, thymol blue, tropeolin OO, quinaldine red, α-dinitrophenol, methyl yellow; dimethyl yellow, bromophenol blue, tetrabromophenol blue, bromochlorophenol blue, Congo red, methyl orange, p-ethoxychrysoidine hydrochloride, napthyl red, alizarin sodium sulfonate, bromocresol green, γ-dinitrophenol, methyl red, lacmoid, chlorophenol red, benzoyl auramine G, bromocresol purple, bromophenol red, p-nitrophenol, bromthymol blue, phenol red, p-quinonemono(bis-4-oxyphenylmethide), neutral red, quinoline blue, α-naphtholphthalein, tropeolin OOO; α-napthol orange, ethyl bis(2,4-dinitrophenyl)acetate, di-o-cresolphthalide, phenolphthalein, thymolphthalein, dimethyl-phenolphthalein, alizarin yellow GG; salicyl yellow, alizarin yellow R, Nile blue, 2,4,6-trinitrophenylmethyl-nitramine, tropeolin O, triphenylrosaniline sulfonic acid (sodium or potassium salt), indigo carmine, nitrobenzene, bromcresol green, bromcresol purple, bromchlorophenol blue, brilliant yellow, brilliant blue R, brilliant cresyl blue ALD, brilliant blue G, brlliant black BN, bromthymol blue, bromphenol red, bromphenol red, bromoxylenol blue, coomasie blue, azolitmin, litmus, pyrogallosulfonphthalein, pyrogallo red-molybdate, alcohol dehydrogenase, ABTS (2,2'-azinobis(3-ethylbenzothiazoline-6-sulfonic acid)), 4-aminoantipyrine (4AAP), tetramethylbenzidine (TMB), o-phenylenediamine (OPD), o-dianisidine, 5-aminosalicylic acid (5AS), 3,3'-diaminobenzidine (DAB), 3-amino-9-ethylcarbazole (AEC), 4-chloro-1-napthol (4C1N), AEC (3-Amino-9-ethyl carbazole), dimethyl-2,5-dihydroperoxyhexane, Bis{4-[N-(3'-sulfo-n-propyl)-N-n-ethyl]amino-2,6-dimethylphenyl}methane (Bis-MAPS), N-Ethyl-N-(2-hydroxy-3-sulfopropyl)-3-methoxyaniline (ADOS), N-Ethyl-N-(3-sulfopropyl)-3-methoxyaniline (ADPS), N-Ethyl-N-(2-hydroxy-3-sulfopropyl)aniline (ALOS), N-Ethyl-N-(3-sulfopropyl)-3,5-dimethylaniline (MAPS), N-Ethyl-N-(2-hydroxy-3-sulfopropyl)-3-methylaniline (TOOS), N-Ethyl-N-(3-sulfopropyl)-3-methylaniline (TOPS), N-(3-sulfopropyl)aniline (HALPS), N-Ethyl-N-(2-hydroxy-3-sulfopropyl)-3,5-dimethoxy-aniline (DAOS), N-Ethyl-N-(3-sulfopropyl)-3,5-dimethoxyaniline (DAPS), N-Ethyl-N-(3-sulfopropyl)aniline (ALPS), N-(2-hydroxy-3-sulfopropyl)-3,5-dimethoxyaniline (HDAOS), N-(3-sulfopropyl)-3,5-dimethoxyaniline (HDAPS), N-Ethyl-N-(2-hydroxy-3-sulfopropyl)-3,5-dimethylani line (MAO), N,N-Bis(4-sulfobutyl)-3,5-dimethylaniline (MADB), pyrogallol, 2,4-Dichlorophenol, N,N-Diethyl-m-toluidine, p-Hydroxybenzene Sulfonate, N,N-Dimethylaniline, 3,5-Dichloro-2-Hydroxybenzenesulfonate, 2,4,6-tribromo-3-hydroxybenzoic acid, Sodium N-Ethyl-N-(3-Sulfopropyl)-m-Anisidine, hydroxybenzoic acid, 4-hydroxybenzoic acid, N-Ethyl-N-(2-hydroxy-3-Sulfopropyl)-m-toluidine, AEC (3-Amino-9-ethyl carbazole), 2-5, dimethyl-2,5-dihydroperoxyhexane, Bis{4-[N-(3'-sulfo-n-propyl)-N-n-ethyl]lamino-2,6-dimethylphenyl}methane (Bis-MAPS), N-Ethyl-N-(2-hydroxy-3-sulfopropyl)-3-methoxyaniline (ADOS), N-Ethyl-N-(3-sulfopropyl)-3-methoxyaniline (ADPS), N-Ethyl-N-(2-hydroxy-3-sulfopropyl)aniline (ALOS), N-Ethyl-N-(3-sulfopropyl)-3,5-dimethylaniline (MAPS), N-Ethyl-N-(2-hydroxy-3-sulfopropyl)-3-methylaniline (TOOS), N-Ethyl-N-(3-sulfopropyl)-3- methylaniline (TOPS), N-(3-sulfopropyl)aniline (HALPS), N-Ethyl-N-(2-hydroxy-3-sulfopropyl)-3,5-dimethoxyaniline (DAOS), N-Ethyl-N-(3-sulfopropyl)-3,5-dimethoxyaniline (DAPS), N-Ethyl-N-(3-sulfopropyl) aniline (ALPS), N-(2-hydroxy-3-sulfopropyl)-3,5-dimethoxyaniline (HDAOS), N-(3-sulfopropyl)-3,5-dimethoxyaniline (HDAPS), N-Ethyl-N-(2-hydroxy-3-sulfopropyl)-3,5-dimethylaniline (MAO), N,N-Bis(4-sulfobutyl)-3,5-dimethylaniline (MADB), 3-Methyl-2-benzothiazolinonehydrazone, Dimethylaniline, 5-bromo-6-chloro-3-indoxyl-beta-D-galacatopyranoside, 4-Aminophenyl-beta-D-galactopyranoside, 3-indoxyl-beta-D-galactopyranoside (blue), 5-Bromo-4-chloro-3-indoxyl-beta-D-galactopyranoside (blue), 5-Bromo-3-indoxyl-beta-D-galactopyranoside (blue), 6-chloro-3-indoxyl-beta-D-galactopyranoside (salmon), 6-Fluoro-3-indoxyl-beta-D-galactopyranoside, 8-Hydroxyquinoline-beta-D-galactopyrano-side, 5-Iodo-3-indoxyl-beta-D-galactopyranoside (purple), N-Methylindoxyl-beta-D-galactopyranoside, 2-Nitrophenyl-beta-D-galactopyranoside, 4-Nitrophenyl-beta-D-galactopyranoside, Naphthol AS-BI-beta-D-galactopyranoside, 2-Naphthyl-beta-D-galactopyranoside (yellow), 4-Methylumbelliferyl-beta-D-glucuronic acid, beta-D-Galactosidase, Iodo-3-indoxyl-beta-D-galactopyranoside, alpha-L-Galactosidase, Iodo-3-indoxyl-alpha-L-beta-Galactosidase, glycosidase, beta-Cellobiosidase, cellobioside, beta-D-Cellobiosidase, 5-Bromo-4-chloro-3-indoxyl-beta-D-cellobioside, 5-Bromo-6-chloro-3-indoxyl-beta-D-cellobioside, 4-Nitrophenyl-beta-D-cellobioside, 1-Naphthyl-cellobioside, 4-Methylumbelliferyl-beta-D-cellobioside, Arabinosidase, Fucosidase, Galactosaminidase, Glucosaminidase, Glucosidase, Glucuronidase, Lactosidase, Maltosidase, Mannosidase, and Xylosidase. Their corresponding substrates, Arabinopyranoside, Fucopyranoside, Galactosaminide, Glucosaminide, Glucopyranoside, Glucuronic acid, Lactopyranoside, Maltopyranoside, Mannopyranoside, Xylopyranoside, 5-Bromo-4-chloro-3-indoxyl, 5-Bromo-6-chloro-3-indoxyl, 6-chloro-3-indoxyl, 5-Bromo-3-indoxyl, 5-Iodo-3-indoxyl, 3-indoxyl, 2-(6-Bromonaphthyl), 6-Fluoro-3-indoxyl 2-Nitrophenyl, 4-Nitrophenyl, 1-Naphthyl, Naphthyl AS-BI, 2-Nitrophenyl-N-acetyl, 4-Nitrophenyl-N-acetyl, 4-Methylumbelliferyl, glycosidase enzyme, carboxyl esterase, cholesterol esterase, sulfatases (e.g. Aryl sufatase), phosphatases (e.g. Alkaline phosphatase), carboxyl esterase, 6-chloro-3-indoxyl butyrate, aryl sulfatase, 5-bromo-4-chloro-3-indoxyl sulfate, alkaline phosphatase, and 2-naphthyl phosphate. It is understood that the present arts discovery of the use of indicators such as the ones mentioned above or others that have not been mentioned that are sensitive to GHB or GBL biological matrices such as urine and other fluids are capable of producing a detectable response in the presence of GHB or GBL are within the present art. Therefore the use of GHB or GBL indicators that are not mentioned here would fall within the spirit and scope of the present invention. These indicators form indicator-complexes with GHB or GBL for determining the presence or amount of gamma-hydroxybutyrate or gamma-butyrolactone in a sample, said method(s) comprising contacting said sample with an indicator which specifically binds to gamma-hydroxybutyrate or gamma-butyrolactone to form an indicatorcomplex; and, measuring said indicatorcomplex to determine the presence or amount of said gamma-hydroxybutyrate or gamma-butrylactone in said sample.

This new art formula will require appropriate buffering. Suitable buffers may include any of the following (referred to here by their commonly used acronyms): citrate, borate, borax, sodium tetraborate decahydrate, sodium perchlorate, sodium chlorate, sodium carbonate, TRIS (Tris[hydroxymethyl]aminomethane), MES (2-[N-Morpholino]ethanesulfonic acid), BIS-TRIS (bis[2-Hydroxyethyl]iminotris[hydroxymethyl]methane; 2-bis[2-Hydroxyethyl]amino-2-[hydroxymethyl-1,3-propanediol), ADA (N-[2-Acetamidol]-2-iminodiacetic acid; N-[Carbaoylmethyl]iminodiacetc acid), ACES (2-[(2-Amino-2-oxoethyl)amino]ethanesulfonic acid; N-[2-Acetamido]-2-aminoethanesulfonic acid), PIPES (PiperazineN-N'-bis[2-ethanesulfonic acid)]; 1,4-Piperzinedethanesulfoic acid), MOPSO (3-[N-Morpholinol]-2-hydroxypropanesulfonic acid), BIS-TRIS PROPANE (1,3-bis[tris(Hydroxymethyl)methylamino]propane), BES (N,N-bis[2-Hydroxyethyl]-2-aminoethaesulfonic acid; 2-bis(2-Hydroxyethyl)amino]ethanesulfonic acid), MOPS (3-[N-Morpholino]propanesulfonic acid), TES (N-tris[Hydroxymethyl]methyl-2-aminomethanesulfonic acid; 2[2-Hysroxy-1,1-bis(hydroxymethyl)-ethyl]amino)ethanesulfonic acid), HEPES (N-[2-Hydroxyethyl]piperazine-N'-[2-ethanesulfonic acid]), DIPSO (3-[N,N-bis(2-Hydroxyethyl)amino]-2-hydroxypropanesulfonic acid), TAPSO (3-[N-tris(Hydroxyethyl)methylamino]-2-hydroxypropanesulfonic acid), HEPPSO (N-[2-Hydroxythyl]piperazine-N'-[2Hydroxypropanesulfonic acid]), POPSO (Piperazine-N,N'-bis[2-hydroxypropanesulfonic acid]), EPPS (N-[2-Hydroxyethyl]piperazine-N'-[3-propanesulfonic acid), TEA (triethanolamine), TRICINE (N-tris[Hydroxymethyl]methyllycine; N-[2-Hydroxy-1-1-bis(hydroxymethyl)etyyl]glycine), BICINE (N,N-bis[2-Hydroxyethyl]glycine), TAPS (N-tris[Hydroxymethyl]methyl-3-aminopropanesulfonic acid; ([2-Hdroxy-1,1-bis(hydroxymethyl)ethyl]arnino)-1-propanesulfonic acid), AMPSO (3-[(1,1-Dimethyl-2-hydroxyethyl)amino]-2-hydroxypropanesulfonic acid), CHES (2-[N-Cyclohexylamino]ethanesulfonic acid), CAPSO (3-[Cyclohexylamino]-2-hydroxy-1-propanesulfonic acid), AMP 2-Amino-2-ethyl-1-propanol, CAPS (3-[cyclohexylamino]-1-propanesulfdnic acid), hydrochloric acid, phosphoric acid, lactic acid, sulfuric acid, nitric acid, chromic acid, boric acid, perchloric acid, potassium hydrogen tartrate, potassium hydrogen phthalate, calcium hydroxide, phosphate, bicarbonate, sodium hydroxide, potassium hydroxide, oxalate or succinate. Other buffers with an effective pK and pH range, and capacity suitable for maintaining the sample-reagent mixture within the required parameters of the assay's reaction mechanism may be added to the above group.

Manufacture of the dry chemistry dipsticks may require the addition of thickeners as taught in the art. Some compounds commonly used for this purpose include: polyvinylpyrrolidone, algin, carragenin, casein, albumin, methyl cellulose, and gelatin. The typical range of concentration for these thickeners is about 0.5 to 5.0 g. per 100 ml. Wetting agents or surfactants are also typically used in dry chemistry. For dry chemistry applications, wetting agents aid in even distribution of the chemicals and promote even color development. Acceptable wetting agents can be hydrophilic polymers, or cationic, anionic, amphoteric, or non-ionic species. Some commonly used wetting agents include sodium dodecyl-benzene sulphonate, sodium lauryl sulphate, benzalkonium chloride, N-lauroylsarcosine sodium salt, Brij-35, Tween 20, Triton X-100, dioctyl sodium sulphosuccinate, and polyethylene glycol 6000. Wetting agents can be added to dipstick impregnation solutions in amounts of 0.5% to 5.0%, and 0.1% to 1.0% in liquid reagents.

Color enhancers may be used such as sucrose, lactose, glucose or other compounds. Color enhancement can be defined as intensification and/or alteration in some manner the color that is produced by the reaction to improve the measurement of the detectable response.

The production of dry chemistry test strips for the present invention can utilize any form of absorbent, solid phase carrier including filter paper, cellulose or synthetic resin fleeces in conjunction with liquid solutions of reagent compositions in volatile solvents. This can be carried out in one or more impregnation steps. Each impregnation may contain one or more of the chemical compounds making up the assay reagent composition; the exact procedure is dictated by the inter-reactivity of the assay constituents and the order in which they may have to react with the analyte of interest.

In the case of the DLFH, the lateral flow invention it can utilize any form of absorbent, solid phase carrier that is capable of transporting a fluid. These can include filter paper, cellulose or synthetic resins. More specifically, the lateral flow material can include cellulose, cellulose acetate, nitrocellulose, mixed ester, teflon, polyvinylidene difluoride (PVDF), polytetrafluoroethylene (PTFE), polysulfone, cotton linter, non-woven rayon, glass fiber, nylon, ion exchange or other suitable membranes or solid support.

After impregnation, the dipsticks are dried, cut into strips, glued to a support structure (usually a flexible, flat, plastic stick made up of polystyrene, vinyl polypropylene, and polyester or other suitable support material) as part of a "sandwich" composed of the handle, test pad, and a synthetic resin film and/or a fine-mesh material in the manner described in German Pat. No, 2,118,455. In addition, the instant invention may be combined with the water-stable film as taught in U.S. Pat. No. 3,530,957 to produce a dipstick in which the excess sample fluid can be wiped off in order to improve the accuracy and precision of the results.

The sensitivity of the assay can be as low as 5 ug/mL, is the cutoffs illustrated in the present art are merely illustrative. The cutoff of 50.0 ug/mL is used because this is the range that an analgesic (high) effect is felt by the user or victim.

The following examples are provided to further illustrate the inventive aspects of the present discovery, and to further exemplify preferred embodiments. As such, they are intended as merely illustrative, and are not to be construed as limiting the scope of the claims appended hereto.

EXAMPLE 1

This is a method for manufacturing a dry chemistry dipstick (DCD, test strip) with a solid carrier for the detection of GHB in urine samples.

Filter paper is successively impregnated with the following solutions and dried at 25 degree C.:

Solution I

Tris-Base (Tris[hydroxymethyl]aminomethane) buffer 2.97 g

NAD 0.3 M distilled water added to 100 mL total volume of solution pH the solution to a value between 1.0 and 12.5 preferably 8.0 lab notes: Buffer strength is preferably 10 mM or greater

Solution 2 hydroxybutyrate dehydrogenase 5 mM

Tris-HCI (Tris[bydroxymethyl]aminomethane hydrochloride) buffer 0.01M

NBT (nitro blue tetrazolium) 0.01 mg/L distilled water added to make 1000 mL total volume of solution lab notes: pH the solution to a value between 1.0 and 12.5 preferably 8.0

In this example a dipstick was prepared in accordance with the instant invention. The device comprised a paper carrier or solid matrix incorporated with the composition of solutions 1 and 2 above. Note that the concentrations of any of the following examples can be varied to suit the dipstick device format (dependent upon paper type, or use of semipermeable membrane or other suitable material). This example is carried out using the following procedure. To produce the test means, a piece of Whatman 3 MM filter paper having approximate dimensions of 1 inch by 3 inches was impregnated with solution 1 by immersing the paper into solution 1. The paper was then dried by using forced air not exceeding 25° C. A second piece of Whatman 1 MM filter paper having approximate dimensions of 1 inch by 3 inches was impregnated with solution 2 by immersing the paper into solution 2. The paper was then dried by using forced air not exceeding 25° C. The dried papers are then laminated to each other by the use of a non-reactive (neutral adhesive). The dried, laminated papers are then applied to one side of a piece of double-sided adhesive transfer tape commercially available from 3M Company, St. Paul, Minn. 55144. The laminate is then slit into portions measuring 3 inches by 0.2 inches. One portion is then attached, via the unused adhesive side to a polystyrene sheet measuring about 1.5 inches by 3 inches and the resulting laminate is slit parallel to its short dimension to form test devices comprising a 1.5 inch oblong polystyrene strip carrying a square of the impregnated papers at one end, the other end serving as the handle. When the dipstick thus obtained is dipped into a urine (note: other sample matrices including saliva, sweat extracts, serum, hair homogenates, gastric contents, cerebral spinal fluid, blood and fluids such as beverages to included but not limited to water, soft drinks, beer, or mixed drinks) will produce no uniform blue color development if no GHB is present. Conversely, if any concentration of GHB is present in the urine at a 0.1% v/v or greater a blue color will develop thus confirming the presence of GHB.

In summary, Example 1 is as follows: the foregoing dry chemistry test strip (dipstick) method for the GHB detection of in a sample of urine comprises the steps of preparing a test means by successively impregnating a solid, carrier matrix with reagent solutions, drying the impregnated, solid test means, then dipping said dried test means into urine, and finally observing any color change in the presence or absence of GHB.

The following changes to the above reagent solutions will remain within the scope and function of this invention and will have similar results to the example above. The GHB indicator reactive compound (reactive in this sense means that hydroxybutyrate dehydrogenase is sensitive the presence of GHB and will react with GHB during which NAD is reduced to NADH) in solution 1 is hydroxybutyrate dehydrogenase, which could be substituted with one or more of the following compounds including hydroxybutyrate dehydrogenase, esterase, 3-hydroxybutyrate dehydrogenase, 4-hydroxybutyrate dehydrogenase, carboxyl esterase, carboxylic-ester hydrolase, β-hydroxybutyrate dehydrogenase, [R]-3-hydroxybutanoate, NAD (nicotinamide adenine dinucleotide)$^+$ oxidoreductase, and α-hydroxybutyrate dehydrogenase, anti-gammahydroxybutyrate, alpha-nicotinamide adenine dinucleotide phosphate, beta-nicotinamide adenine dinucleotide phosphate and all analogs of the afore mentioned.

The indicator NBT, which will develop color in the presence of the reduction of NAD or NADPH can be replaced by one of the following: phenazine methosulfate, tetranitroblue tetrazolium, napthol AS-TR phosphate, methylene blue, Fast red, napthol-AS-MX, napthol AS-TR phosphate or analogs thereof.

The Tris buffer in solution 1, may be substituted with one or more of the following buffers: citrate, borate, borax, sodium tetraborate decahydrate, sodium perchlorate, sodium chlorate, sodium carbonate, MES (2-[N-Morpholino] ethanesulfonic acid), BIS-TRIS (bis[2-Hydroxyethyl] iminotris[hydroxymethyl]methane; 2-bis[2-Hydroxyethyl] amino-2-[hydroxymethyl-1,3-propanediol), ADA (N-[2-Acetamidol]-2-iminodiacetic acid; N-[Carbaoylmethyl] iminodiacetc acid), ACES (2-[(2-Amino-2-oxoethyl)amino] ethanesulfonic acid; N-[2-Acetamido]-2-aminoethanesulfonic acid), PIPES (PiperazineN-N'-bis[2-ethanesulfonic acid)]; 1,4-Piperzinedethanesulfoic acid), MOPSO (3-[N-Morpholinol]-2-hydroxypropanesulfonic acid), BIS-TRIS PROPANE (1,3-bis[tris(Hydroxymethyl) methylarnino]propane), BES (N,N-bis[2-Hydroxyethyl]-2-aminoethaesulfonic acid; 2-bis(2-Hydroxyethyl)amino] ethanesulfonic acid), MOPS (3-[N-Morpholino] propanesulfonic acid), TES (N-tris[Hydroxyrnethyl]methyl-2-aminomethanesulfonic acid; 2[2-Hysroxy-1,1-bis (hydroxymethyl)-ethyl]amino)ethanesulfonic acid), HEPES (N-[2-Hydroxyethyl]piperazine-N'-[2-ethanesulfonic acid]), DIPSO (3-[N,N-bis(2-Hydroxyethyl)amino]-2-hydroxypropanesulfonic acid), TAPSO (3-[N-tris (Hydroxyethyl)methylamino]-2-hydroxypropanesulfonic acid), HEPPSO (N-[2-Hydroxythyl]piperazine-N'-[2Hydroxypropanesulfonic acid]), POPSO (Piperazine-N, N'-bis[2-hydroxypropanesulfonic acid]), EPPS (N-[2-Hydroxyethyl]piperazine-N'-[3-propanesulfonic acid), TEA (triethanolamine), TRICINE (N-tris[Hydroxymethyl] methyllycine; N-[2-Hydroxy-1-1-bis(hydroxymethyl)etyyl] glycine), BICINE (N,N-bis[2-Hydroxyethyl]glycine), TAPS (N-tris[Hydroxymethyl]methyl-3-aminopropanesulfonic acid; ([2-Hdroxy-1,1-bis(hydroxymethyl)ethyl]amino)-1-propanesulfonic acid), AMPSO (3-[(1,1-Dimethyl-2-hydroxyethyl)amino]-2-hydroxypropanesulfonic acid), CHES (2-[N-Cyclohexylamino]ethanesulfonic acid), CAPSO (3-[Cyclohexylamino]-2-hydroxy-1-propanesulfonic acid), AMP 2-Amino-2-ethyl-1-propanol, CAPS (3-[cyclohexylamino]-1-propanesulfonic acid), hydrochloric acid, phosphoric acid, lactic acid, sulfuric acid, nitric acid, chromic acid, boric acid, perchloric acid, potassium hydrogen tartrate, potassium hydrogen phthalate, calcium hydroxide, phosphate, bicarbonate, sodium hydroxide, potassium hydroxide, oxalate or succinate. Other buffers with an effective pK and pH range, and capacity suitable for maintaining the sample-reagent mixture within the required parameters of the assay's reaction mechanism may be added to the above group.

EXAMPLE 2

This is a method for manufacturing a liquid, carrier-free reagent for the adulteration detection of GHB in samples submitted for drugs of abuse analysis.
Prepare a Solution Containing:
Solution I (RI)
Tris-Base (Tris[hydroxymethyl]aminomethane) buffer 2.97 g
NAD 0.3 M
hydroxybutyrate dehydrogenase 5 mM
distilled water added to make 1000 mL total volume of solution lab notes: a) pH the solution to a value between 1.0 and 12.5 preferably 8.0
b) Buffer strength is preferably 0.01 Molar or greater
c) NBT needs to be in solution at a concentration 0.001 mg/L or greater GHB Calibrator Formulations
Zero (0) calibrator:
1 liter of 0.2 micron filtered normal human urine with no adulterants or drugs
present, and 0.01% sodium azide.*
50 ug/mL calibrator:
50 ug/mL GHB
0.01 M Sodium Borate
100 mL of 0.2 micron filtered normal human urine with no adulterants or drugs present*
pH the solution to a value between 3.0 and 11.0 preferably 9.0.
lab notes:* Human urine can be substituted with distilled water, synthetic urine or other suitable solvent. The bacterial inhibitor sodium azide could be replaced with chloroamphenicol or other suitable bacterial inhibitors that would inhibit the growth of bacteria.

The reagent system of the instant invention (liquid reagent) is intended for use on any automatic chemistry analyzers with open channel capability including Olympus series, Hitachi 700 series, Beckmans and many others. The reagent as outlined in Example 2 is used in the following manner: the one component of the reagent composition (R-1) is placed in the reagent compartment of the analyzer; samples, calibrators, and controls are aliquoted into sample cups which are then placed on the analyzer. An aliquot of 5 uL of each specimen is then pipetted into a single, discrete cuvette followed by the addition of 150 uL of the first reagent, R-1, and mixed; A first spectrophotometer reading is then taken followed by a second after a specified incubation period (i.e. one minute for this example) at the specified wavelength (between 340 and 800 nm). The spectrophotometer readings are then recorded. In this instance the assay is read at 340 nm. It is noted that at this wavelength that the conversion (reduction) of NAD to NADH is observed. The absorbance of samples, and controls are printed and then compared to the calibrator's absorbance. The quantitative value for GHB concentration is then calculated. Any concentration of GHB greater than 50.0 ug/mL is considered positive for the presence of GHB.

Please note if the present art is not used as illustrated that very significant increase in the cost of analysis, because a GC-MS assay must then be performed to verify the presence of GHB. The GC-MS analysis costs 100 times as much as the screen ($100 vs $1). Every additional unnecessary GC-MS performed drives up the overall cost of drug testing. Eliminating these additional, unnecessary assays will save millions of dollars per year.

Specifications for running urine samples vary from instrument to instrument. Listed below is an example of parameters for the Hitachi 700 series analyzer. The settings are intended as guidelines, and are set forth with the understanding that all those skilled in the art would recognize that such parameters will vary from instrument to instrument. The suggested specifications for the Hitachi 700 series are as follows:

| Parameter settings for the Hitachi 700 series | |
|---|---|
| Test: | [GHB] |
| Assay code: | [1 POINT] [50] - [0] |
| Sample volume: | [5] [5] |
| R1 volume | [150] [100] [NO] |
| R2 volume | [0] [100] [NO] |
| Wavelength | [0] [340] |
| Calib. Method: | [Linear] [0] [0] |
| Std. (1) Conc.-POS: | [0.0] *–[1]* assigned calibrator value |
| Std. (2) Conc.-POS: | [50.0] –[2] assigned calibrator value |
| Std. (3) Conc.-POS: | [ ] - [ ] |
| Std. (4) Conc.-POS: | [ ] - [ ] |
| Std. (5) Conc.-POS: | [ ] - [ ] |
| Std. (6) Conc.-POS: | [ ] - [ ] |
| SD Limit: | [999] |
| Duplicate Limit: | [32000] |
| Sensitivity Limit: | [0] |
| ABS. Limit (INC/DEC): | [32000] [INCREASE] |
| Prozone Limit: | [0] [lower] |
| Expected Value: | [0.0] - [1.0] |
| Tech. Limit: | [0] - [1000] |
| Instrument Factor | [1.0] |

Note: this assay is to be performed at the same temperature used for the DAU testing, usually 37 degrees Centigrade. However, this can vary without affecting the assay. The temperature could be between refrigerated to 45 degrees Centigrade.

Thus as described above, an unknown urine submitted for drugs of anaylsis for GHB will produce a value of less than the 0.0 ug/mL if no GHB is present. Conversely, if the sample has a concentration of greater than 50.0 ug/mL than the sample is positive for GHB.

To summarize more specifically Example 2, the automated method for the detection of adulteration of an unknown sample of urine submitted for drugs of abuse testing comprising the steps of placing aliquots of an unknown urine (or other biological sample i.e. serum, whole blood, cerebral spinal fluid, gastric fluid, hair homogenates, sweat extracts, saliva or other biological fluid and other fluids such as beverages, water, etc.) and calibrator to be tested in automated analyzer sampling cups, placing the cups in a sampling tray within an automated analyzer, transferring the aliquots of sample and calibrator to cuvettes mounted within the automated analyzer, injecting a first reagent composition (R-1) comprising an indicator and buffer in an aqueous medium into the cuvettes, and mixing sample and reagents, and reading absorbance values of reaction mixture composed of reagents and test samples (said test samples include urine specimens, controls, and calibrator) at specified intervals, in accordance with a preprogrammed code introduced into the automated analyzer, at a preprogrammed monochromatically specified wavelength, and comparing absorbance of the first reagent composition plus the unknown samples with that of the first reagent composition plus the calibrator containing a zero reference point (normal urinary matrix), and thereby determining quantitatively the presence or absence of GHB.

The following changes to the above reagent solutions will remain within the scope and function of this invention and will have similar results to the example above. The indicator in the solution 1, GHB, which is the indicator reactive compound (reactive in this sense means that hydroxybutyrate dehydrogenase is sensitive the presence of GHB and will react with GHB during which NAD is reduced to NADH) in solution 1 is hydroxybutyrate dehydrogenase, which could be substituted with one or more of the following compounds including esterase, 3-hydroxybutyrate dehydrogenase, 4-hydroxybutyrate dehydrogenase, carboxyl esterase, carboxylic-ester hydrolase, β-hydroxybutyrate dehydrogenase, [R]-3-hydroxybutanoate, NAD (nicotinamide adenine dinucleotide)$^+$ oxidoreductase, and α-hydroxybutyrate dehydrogenase, anti-gamma-hydroxybutyrate, alpha-nicotinamide adenine dinucleotide phosphate, beta-nicotinamide adenine dinucleotide phosphate and all analogs of the afore mentioned.

The Tris buffer in solution 1, may be substituted with one or more of the following buffers: citrate, borate, borax, sodium tetraborate decahydrate, sodium perchlorate, sodium chlorate, sodium carbonate, MES (2-[N-Morpholino] ethanesulfonic acid), BIS-TRIS (bis[2-Hydroxyethyl] iminotris[hydroxymethyl]methane; 2-bis[2-Hydroxyethyl] amino-2-[hydroxymethyl-1,3-propanediol), ADA (N-[2-Acetamidol]-2-iminodiacetic acid; N-[Carbaoylmethyl] iminodiacetc acid), ACES (2-[(2-Amino-2-oxoethyl)amino] ethanesulfonic acid; N-[2-Acetamido]-2-aminoethanesulfonic acid), PIPES (PiperazineN-N'-bis[2-ethanesulfonic acid)]; 1,4-Piperzinedethanesulfoic acid), MOPSO (3-[N-Morpholinol]-2-hydroxypropanesulfonic acid), BIS-TRIS PROPANE (1,3-bis[tris(Hydroxymethyl) methylamino]propane), BES (N,N-bis[2-Hydroxyethyl]-2-aminoethaesulfonic acid; 2-bis(2-Hydroxyethyl)amino] ethanesulfonic acid), MOPS (3-[N-Morpholino] propanesulfonic acid), TES (N-tris[Hydroxymethyl]methyl-2-aminomethanesulfonic acid; 2[2-Hysroxy-1,1-bis (hydroxymethyl)-ethyl]amino)ethanesulfonic acid), HEPES (N-[2-Hydroxyethyl]piperazine-N'-[2-ethanesulfonic acid]), DIPSO (3-[N,N-bis(2-Hydroxyethyl)amino]-2-hydroxypropanesulfonic acid), TAPSO (3-[N-tris (Hydroxyethyl)methylamino]-2-hydroxypropanesulfonic acid), HEPPSO (N-[2-Hydroxythyl]piperazine-N'-[2Hydroxypropanesulfonic acid]), POPSO (Piperazine-N, N'-bis[2-hydroxypropanesulfonic acid]), EPPS (N-[2-Hydroxyethyl]piperazine-N'-[3-propanesulfonic acid), TEA (triethanolamine), TRICINE (N-tris[Hydroxymethyl] methyllycine; N-[2-Hydroxy-1-1-bis(hydroxymethyl)etyyl] glycine), BICINE (N,N-bis[2-Hydroxyethyl]glycine), TAPS (N-tris[Hydroxymethyl]methyl-3-aminopropanesulfonic acid; ([2-Hdroxy-1,1-bis(hydroxymethyl)ethyl]amino)-1-propanesulfonic acid), AMPSO (3-[(1,1-Dimethyl-2-hydroxyethyl)amino]-2-hydroxypropanesulfonic acid), CHES (2-[N-Cyclohexylamino]ethanesulfonic acid), CAPSO (3-[Cyclohexylamino]-2-hydroxy-1-propanesulfonic acid), AMP 2-Amino-2-ethyl-1-propanol, CAPS (3-[cyclohexylamino]-1-propanesulfonic acid), hydrochloric acid, phosphoric acid, lactic acid, sulfuric acid, nitric acid, chromic acid, boric acid, perchloric acid, potassium hydrogen tartrate, potassium hydrogen phthalate, calcium hydroxide, phosphate, bicarbonate, sodium hydroxide, potassium hydroxide, oxalate or succinate. Other buffers with an effective pK and pH range, and capacity suitable for maintaining the sample-reagent mixture within the required parameters of the assay's reaction mechanism may be added to the above group, however acidic buffers are preferred.

EXAMPLE 3

This example will illustrate in detail the exact method for manufacturing the lateral flow GHB method. Keep in mind this method could be utilized for any general chemistry "test pad" or pads that are currently used or will be used in the art. In the case of DLFH technology, the manufacturing process includes impregnating onto an absorbent, solid carrier (e.g. paper) called in this example, the "test pad", in exactly the same manner as Example 1 with similar constituents. The test pad, once impregnated, is dried, then mounted onto a solid support (nitrocellulose membrane) that is capable of transporting (through lateral flow) liquid to the test pad from the point of application of a test sample. In simpler terms, the device is dipped into a liquid or the liquid sample is placed on the device at the bottom or starting point for the assay. The liquid migrates from the starting application point to the opposite end of the nitrocellulose lateral flow paper, during which the test pad becomes saturated with the sample. The reaction takes place on the test pad and color develops. The developed color is then compared to a color chart with known concentrations of GHB that has the appropriate colors relative to each specific concentration of GHB(s). For example a specific color for 0.0 ug/mL GHB, 50.0 ug/mL, 100.0 ug/mL, etc., for comparison. The results are then recorded. Note, the test pad must be an absorbent (wicking) material that permits migration of sample up the solid absorbent test pad and allows analytes and reactants to interact.

Absorbent material is successively impregnated with the following solutions and dried at 25 degree C.:
Solution 1
  NAD 0.3 M
  hydroxybutyrate dehydrogenase 5 mM
  Tris-HCI (Tris[hydroxymethyl]aminomethane hydrochloride) buffer 0.00M
  NBT (nitro blue tetrazolium) 0.01 mg/L
  distilled water added to 100 mL total volume of solution
  pH the solution to a value between 1.0 and 12.5 preferably 8.0
  lab notes: Buffer strength is preferably 10 mM or greater In this example, the lateral flow device is prepared in accordance with the instant invention. The lateral flow device is comprised of a paper carrier matrix (S&S, 593 grade filter paper) impregnated with the compositions of solution 1. The paper is then cut into test pads 5 mm by 5mm. Note that said concentrations of any of the above constituents can be varied to suit the DLFH lateral flow/dipstick device format (e.g. dependent upon paper type, and inclusion of semi-permeable membranes or other innovations utilized in dry chemistry technology). The paper is then dried using forced air. The dried impregnated test pad is then placed at approximately 35 mm (in the middle) of a 5 mm wide by 70 mm long nitrocellulose membrane (S&S Fast-Track® NC) and makes fluid contact with nitrocellulose lateral flow paper. The nitrocellulose membrane is capable of transporting a liquid by capillary action or wicking from one end of the lateral flow device to the other in approximately 60 seconds. In this example, the DLFH has the dimensions of 5 mm wide by 70mm long and can be backed by or in contact with strips of glass fiber filter material (e.g. S&S 30 grade) to aid in controlling the wicking action, or other solid support material can be used.

Again, to completely illustrate the present device the starting point or origin at which the sample is placed on the test device is 5 mm from one end of the strip, and 35 mm from the site of where the test pad is placed in fluid contact with the strip. For simplicity, this example will have the 5 mm by 5 mm impregnated test pad placed on top of the lateral flow paper and thus be in fluid contact with the said paper.

The mechanics of how the present art's LFD and dipstick test pad hybrid may be explained is as follows. The starting point or origin at which the sample is placed on the test device is 5 mm from one end of the strip, and 35 mm from site where the chemically impregnated test pad is in fluid contact with the lateral flow paper. The test pad can be placed on top of the lateral flow paper making fluid contact with the lateral flow paper from the bottom side of the test pad, or the lateral flow paper can touch the paper from the side of the test pad and remain in fluid contact with the test pad. Or the lateral flow paper can rest on top of the edge of test pad or be attached and in fluid contact with the test pad in some other manner. One of the novel advantages in using a hybrid device made of lateral flow material and a dry chemistry test pad is the lack of cross contamination from one pad to the next from excessive fluid, as is inherent in the prior art. For illustration, currently there are available many different types of dry chemistry test strips available, such as the Miles Laboratories, Inc. MULTISTIX®. This device and many other like it has multiple reagents test pads with different chemistries impregnated onto each pad on a single support membrane backing (usually plastic). Because of the relative proximity of these pads to each other on the same device it is easy for cross contamination to occur, causing unreliable results. This is called "runover" (i.e. when a reagent from one pad runs over another adjacent test pad). The present arts eliminates runover. The applicants novel approach to the solution of runover has not been taught prior to the present art and is the result of extensive research and development.

Result interpretation can be explained as follows. If the sample is positive, with a concentration of 50.0 ug/mL GHB or more, the following occurs. A drop of urine (approximately 50 uL) is applied at the starting point or origin of the strip. The urine then migrates to the opposite or terminal end of the strip. As the urine migrates across the lateral flow material (nitrocellulose) and comes into contact with the test pad (filter paper), the urine will saturate the pad and cause a chemical reaction between the impregnated chemicals and GHB in the urine. A blue color will develop on the test pad indicating a positive (greater than 50.0 ug/mL GHB) for the presence of high levels of GHB. This color can then be compared to a color chart showing the different colors from colorless (white background)) to a dark blue depending upon the concentration of the GHB(s), if greater than 50.0 ug/mL. The reaction on the test pad is immediate thus the test results can be observed immediately.

If the sample is negative, with a concentration of less than 50.0 ug/mL of GHB present the following occurs. A drop of urine (approximately 50 uL) is applied at the starting point or origin of the strip. The urine then migrates to the opposite or terminal end of the strip. As the urine migrates across the lateral flow material and comes into contact with the test pad, the urine will saturate the pad and cause a chemical reaction between the impregnated chemicals and GHB. However, this example is for a negative result, thus, no reaction occurs and no color develops, indicating a negative result. This negative result color can then be compared to a color chart showing the different colors from no color developed (negative) to dark blue depending upon the concentration of the GHB, if greater than 50 ug/mL GHB. The reaction on the test pad is immediate thus the test results can be observed immediately.

Changes to the above reagent solution of example 3 can be made and still remain within the scope and finction of this invention and will have similar results to examples 1 and 2 above. The indicator(s) and buffer(s) of example 3 can be replaced by all the examples and possible substitutions as illustrated in example 1.

This brief description of the present art illustrates a completely enabled device that would allow an individual, physician, patient, and/or technician to quickly and easily determine the presence of the GHB in urine, providing a much needed advancement the art of GHB testing.

To briefly explain the present device as taught. The present art includes a device for the detection of GHB in a sample of urine submitted for drugs of abuse testing the steps comprise of preparing a dry chemistry test means by successively impregnating a solid, carrier matrix with reagent solutions containing an indicator and a buffer, and drying the impregnated, solid carrier matrix. Finally, by dipping said dry chemistry test means into urine, one can observe the detectable response in the form of a color developed in the presence or absence of GHB. This present art also illustrates a unique device that will prevent cross contamination (runover) of test pads on the same dipstick, as well as a unique dry chemistry test pad lateral flow device hybrid. These methods can incorporate detectable responses in the visible color range to the human eye or in the visible light spectrum. These methods have a wide sample choice other than urine, and can be replaced by any biological sample including serum, whole blood, cerebral spinal fluid, gastric fluid, hair homogenates, sweat extracts, saliva or other biological fluid and other fluids such as water, beverages (beer, soft drinks, etc.), to include alcohol drinks.

EXAMPLE 4

This is a method for manufacturing a dry chemistry dipstick (DCD) test strip with a solid carrier for the detection of GBL in urine samples.

Filter paper is successively impregnated with the following solutions and dried at 25 degree C.:

Solution I
  Hepes buffer 2.97 g
  NAD 0.3 M
  distilled water added to 100 mL total volume of solution
  pH the solution to a value between 1.0 and 12.5 preferably 6.5
  lab notes: Buffer strength is preferably 10 mM or greater Solution 2
  gamma-butyrolactone dehydrogenase 5 mM
  Hepes buffer 0.00M
  NBT (nitro blue tetrazolium) 0.01 mg/L
  distilled water added to make 1000 mnL total volume of solution
  lab notes: pH the solution to a value between 1.0 and 12.5 preferably 6.5

In this example a dipstick was prepared in accordance with the instant invention. The device comprised a paper carrier or solid matrix incorporated with the composition of solutions 1 and 2 above. Note that the concentrations of any of the following examples can be varied to suit the dipstick device format (dependent upon paper type, or use of semipermeable membrane or other suitable material). This example is carried out using the following procedure. To produce the test means, a piece of Whatman 3 MM filter paper having approximate dimensions of 1 inch by 3 inches was impregnated with solution 1 by immersing the paper into solution 1. The paper was then dried by using forced air not exceeding 25° C. A second piece of Whatman 1 MM filter paper having approximate dimensions of 1 inch by 3 inches was impregnated with solution 2 by immersing the paper into solution 2. The paper was then dried by using forced air not exceeding 25° C. The dried papers are then laminated to each other by the use of a non-reactive (neutral adhesive). The dried, laminated papers are then applied to one side of a piece of double-sided adhesive transfer tape commercially available from 3M Company, St. Paul, Minn. 55144. The laminate is then slit into portions measuring 3 inches by 0.2 inches. One portion is then attached, via the unused adhesive side to a polystyrene sheet measuring about 1.5 inches by 3 inches and the resulting laminate is slit parallel to its short dimension to form test devices comprising a 1.5 inch oblong polystyrene strip carrying a square of the impregnated papers at one end, the other end serving as the handle. When the dipstick thus obtained is dipped into a urine (note: other sample matrices including saliva, sweat extracts, serum, hair homogenates, gastric contents, cerebral spinal fluid, blood and fluids such as beverages to included but not limited to water, soft drinks, beer, or mixed drinks) will produce no uniform blue color development if no GBL is present. Conversely, if any concentration of GBL is present in the urine at a 0.1% v/v or greater a blue color will develop thus confirming the presence of GBL.

In summary, Example 4 is as follows: the foregoing dry chemistry test strip (dipstick) method for the GBL detection of in a sample of urine comprises the steps of preparing a test means by successively impregnating a solid, carrier matrix with reagent solutions, drying the impregnated, solid test means, then dipping said dried test means into urine, and finally observing any color change in the presence or absence of GBL.

The following changes to the above reagent solutions will remain within the scope and function of this invention and will have similar results to the example above. The GBL indicator reactive compound (reactive in this sense means that gamma-butyrolactone dehydrogenase is sensitive the presence of GBL and will react with GBL during which NAD is reduced to NADH) in solution 1 is gamma-butyrolactone dehydrogenase, which could be substituted with one or more of the following compounds including NAD (nicotinamide adenine dinucleotide)$^+$, oxidoreductase, anti-GBL, alpha-nicotinamide adenine dinucleotide phosphate, beta-nicotinamide adenine dinucleotide phosphate, ketone group sensitive indicators and all analogs of the afore mentioned.

The indicator NBT, which will develop color in the presence of the reduction of NAD or NADPH can be replaced by one of the following: phenazine methosulfate, tetranitroblue tetrazolium, napthol AS-TR phosphate, methylene blue, Fast red, napthol-AS-MX, napthol AS-TR phosphate or analogs thereof.

The Hepes buffer in solution 1, may be substituted with one or more of the following buffers: citrate, borate, borax, sodium tetraborate decahydrate, sodium perchlorate, sodium chlorate, sodium carbonate, TRIS (Tris[hydroxymethyl] aminomethane, MES (2-[N-Morpholino]ethanesulfonic acid), BIS-TRIS (bis[2-Hydroxyethyl]iminotris [hydroxymethyl]methane; 2-bis[2-hydroxyethyl]amino-2-[hydroxymethyl-1,3-propanediol), ADA (N-[2-Acetamidol]-2-iminodiacetic acid; N-[Carbaoylmethyl] iminodiacetc acid), ACES (2-[(2-Amino-2-oxoethyl)amino] ethanesulfonic acid; N-[2-Acetamido]-2-aminoethanesulfonic acid), PIPES (PiperazineN-N'-bis[2-ethanesulfonic acid)]; 1,4-Piperzinedethanesulfoic acid), MOPSO (3-[N-Morpholinol]-2-hydroxypropanesulfonic acid), BIS-TRIS PROPANE (1,3-bis[tris(Hydroxymethyl) methylamino]propane), BES (N,N-bis[2-Hydroxyethyl]-2-aminoethaesulfonic acid; 2-bis(2-Hydroxyethyl)amino] ethanesulfonic acid), MOPS (3-[N-Morpholino) propanesulfonic acid), TES (N-tris[Hydroxymethyl]methyl-2-aminomethanesulfonic acid; 2[2-Hysroxy-1,1-bis (hydroxymethyl)-ethyl]amino)ethanesulfonic acid), DIPSO (3-[N,N-bis(2-Hydroxyethyl)amino]-2-hydroxy- propane-sulfonic acid), TAPSO (3-[N-tris(Hydroxyethyl) methylamino]-2-hydroxypropanesulfonic acid), HEPPSO (N-[2-Hydroxythyl]piperazine-N'-[2Hydroxypropane-sulfonic acid]), POPSO (Piperazine-N,N'-bis[2-hydroxypropanesulfonic acid]), EPPS (N-[2-Hydroxyethyl] piperazine-N'-[3-propanesulfonic acid), TEA (triethanolamine), TRICINE (N-tris[Hydroxymethyl] methyllycine; N-[2-Hydroxy-1-1-bis(hydroxymethyl)etyyl] glycine), BICINE (N,N-bis[2-Hydroxyethyl]glycine), TAPS (N-tris[Hydroxymethyl]methyl-3-aminopropanesulfonic acid; ([2-Hdroxy-1,1-bis(hydroxymethyl)ethyl]amino)-1-propanesulfonic acid), AMPSO (3-[(1,1-Dimethyl-2-hydroxyethyl)amino]-2-hydroxypropanesulfonic acid), CHES (2-[N-Cyclohexylamino]ethanesulfonic acid), CAPSO (3-[Cyclohexylamino]-2-hydroxy-1-propanesulfonic acid), AMP 2-Amino-2-ethyl-1-propanol, CAPS (3-[cyclohexylamino]-1-propanesulfonic acid), hydrochloric acid, phosphoric acid, lactic acid, sulfuric acid, nitric acid, chromic acid, boric acid, perchloric acid, potassium hydrogen tartrate, potassium hydrogen phthalate, calcium hydroxide, phosphate, bicarbonate, sodium hydroxide, potassium hydroxide, oxalate or succinate. Other buffers with an effective pK and pH range, and capacity suitable for maintaining the sample-reagent mixture within the required parameters of the assay's reaction mechanism may be added to the above group.

EXAMPLE 5

This is a method for manufacturing a liquid, carrier-free reagent for the adulteration detection of GBL in samples submitted for drugs of abuse analysis.
Prepare a Solution Containing:
  Solution I (R1)
  Hepes buffer 2.97 g
  NAD 0.3 M
  gamma-butyrolactone dehydrogenase 5 mM
  distilled water added to make 1000 mL total volume of solution lab notes: a) pH the solution to a value between 1.0 and 12.5 preferably 6.5
  b) Buffer strength is preferably 0.01 Molar or greater
  c) NBT needs to be in solution at a concentration 0.001 mg/L or greater
GBL Calibrator Formulations
  Zero (0)calibrator:
  1 liter of 0.2 micron filtered normal human urine with no adulterants or drugs present, and 0.01% sodium azide.*
  50 ug/mL calibrator:
  50 ug/mL GBL
  0.01 M Tris HCl
  100 mL of 0.2 micron filtered normal human urine with no adulterants or drugs present*
  pH the solution to a value between 3.0 and 11.0 preferably 5.0.
  lab notes:* Human urine can be substituted with distilled water, synthetic urine or other suitable solvent. The bacterial inhibitor sodium azide could be replaced with chloroamphenicol or other suitable bacterial inhibitors that would inhibit the growth of bacteria.

The reagent system of the instant invention (liquid reagent) is intended for use on any automatic chemistry analyzers with open channel capability including Olympus series, Hitachi 700 series, Beckmans and many others. The reagent as outlined in Example 5 is used in the following manner: the one component of the reagent composition (R-1) is placed in the reagent compartment of the analyzer; samples, calibrators, and controls are aliquoted into sample cups which are then placed on the analyzer. An aliquot of 5 uL of each specimen is then pipetted into a single, discrete cuvette followed by the addition of 150 uL of the first reagent, R-1, and mixed; A first spectrophotometer reading is then taken followed by a second after a specified incubation period (i.e. one minute for this example) at the specified wavelength (between 340 and 800 nm). The spectrophotometer readings are then recorded. In this instance the assay is read at 340 nm. It is noted that at this wavelength that the conversion (reduction) of NAD to NADH is observed. The absorbance of samples, and controls are printed and then compared to the calibrator's absorbance. The quantitative value for GBL concentration is then calculated. Any concentration of GBL greater than 50.0 ug/mL is considered positive for the presence of GBL.

Please note if the present art is not used as illustrated that very significant increase in the cost of analysis, because a GC-MS assay must then be performed to verify the presence of GBL. The GC-MS analysis costs 100 times as much as the screen ($100 vs $1). Every additional unnecessary GC-MS performed drives up the overall cost of drug testing. Eliminating these additional, unnecessary assays will save millions of dollars per year.

Specifications for running urine samples vary from instrument to instrument. Listed below is an example of parameters for the Hitachi 700 series analyzer. The settings are intended as guidelines, and are set forth with the understanding that all those skilled in the art would recognize that such parameters will vary from instrument to instrument. The suggested specifications for the Hitachi 700 series are as follows:

| Parameter settings for the Hitachi 700 series | |
| --- | --- |
| Test: | [GBL] |
| Assay code: | [1 POINT] [50] - [0] |
| Sample volume: | [5] [5] |
| R1 volume | [150] [100] [NO] |
| R2 volume | [0] [100] [NO] |
| Wavelength | [0] [340] |
| Calib. Method: | [Linear] [0] [0] |
| Std. (1) Conc.-POS: | [0.0] *-[1]* assigned calibrator value |
| Std. (2) Conc.-POS: | [50.0] -[2] assigned calibrator value |
| Std. (3) Conc.-POS: | [ ] - [ ] |
| Std. (4) Conc.-POS: | [ ] - [ ] |
| Std. (5) Conc.-POS: | [ ] - [ ] |
| Std. (6) Conc.-POS: | [ ] - [ ] |
| SD Limit: | [999] |
| Duplicate Limit: | [32000] |
| Sensitivity Limit: | [0] |
| ABS. Limit (INC/DEC): | [32000] [INCREASE] |
| Prozone Limit: | [0] [lower] |
| Expected Value: | [0.0] - [1.0] |
| Tech. Limit: | [0] - [1000] |
| Instrument Factor | [1.0] |

Note: this assay is to be performed at the same temperature used for the DAU testing, usually 37 degrees Centigrade. However, this can vary without affecting the assay. The temperature could be between refrigerated to 45 degrees Centigrade.

Thus as described above, an unknown urine submitted for drugs of anaylsis for GBL will produce a value of less than the 0.0 ug/mL if no GBL is present. Conversely, if the sample has a concentration of greater than 50.0 ug/mL than the sample is positive for GBL.

To summarize more specifically Example 5, the automated method for the detection of adulteration of an unknown sample of urine submitted for drugs of abuse testing comprising the steps of placing aliquots of an unknown urine (or other biological sample i.e. serum, whole blood, cerebral spinal fluid, gastric fluid, hair homogenates, sweat extracts, saliva or other biological fluid and other fluids such as beverages, water, etc.) and calibrator to be tested in automated analyzer sampling cups, placing the cups in a sampling tray within an automated analyzer, transferring the aliquots of sample and calibrator to cuvettes mounted within the automated analyzer, injecting a first reagent composition (R-1) comprising an indicator and buffer in an aqueous medium into the cuvettes, and mixing sample and reagents, and reading absorbance values of reaction mixture composed of reagents and test samples (said test samples include urine specimens, controls, and calibrator) at specified intervals, in accordance with a preprogrammed code introduced into the automated analyzer, at a preprogrammed monochromatically specified wavelength, and comparing absorbance of the first reagent composition plus the unknown samples with that of the first reagent composition plus the calibrator containing a zero reference point (normal urinary matrix), and thereby determining quantitatively the presence or absence of GBL.

The following changes to the above reagent solutions will remain within the scope and function of this invention and will have similar results to the example above. The indicator in the solution 1, GBL, which is the indicator reactive compound (reactive in this sense means that gamma-butyrolactone dehydrogenase is sensitive the presence of GBL and will react with GBL during which NAD is reduced to NADH) in solution 1 is gamma-butyrolactone dehydrogenase, which could be substituted with one or more of the following compounds including NAD (nicotinamide adenine dinucleotide)$^+$, oxidoreductase, anti-GBL, alpha-nicotinarnide adenine dinucleotide phosphate, beta-nicotinamide adenine dinucleotide phosphate, ketone group sensitive indicators and all analogs of the afore mentioned.

The Hepes buffer in solution 1, may be substituted with one or more of the following buffers: citrate, borate, borax, sodium tetraborate decahydrate, sodium perchlorate, sodium chlorate, sodium carbonate, MES (2-[N-Morpholino] ethanesulfonic acid), BIS-TRIS (bis[2-Hydroxyethyl] iminotris[hydroxymethyl]methane; 2-bis[2-Hydroxyethyl] amino-2-[hydroxymethyl-1,3-propanediol), ADA (N-[2-Acetamidol]-2-iminodiacetic acid; N-[Carbaoylmethyl] iminodiacetc acid), ACES (2-[(2-Amino-2-oxoethyl)amino] ethanesulfonic acid; N-[2-Acetamido]-2-aminoethanesulfonic acid), PIPES (PiperazineN-N'-bis[2-ethanesulfonic acid)]; 1,4-Piperzinedethanesulfoic acid), MOPSO (3-[N-Morpholinol]-2-hydroxypropanesulfonic acid), BIS-TRIS PROPANE (1,3-bis[tris(Hydroxymethyl) methylamino]propane), BES (N,N-bis[2-Hydroxyethyl]-2-aminoethanesulfonic acid; 2-bis(2-Hydroxyethyl)amino] ethanesulfonic acid), MOPS (3-[N-Morpholino] propanesulfonic acid), TES (N-tris[Hydroxymethyl]methyl-2-aminomethanesulfonic acid; 2[2-Hysroxy-1,1-bis (hydroxymethyl)-ethyl]amino)ethanesulfonic acid), TRIS (Tris[hydroxymethyl]aminomethane, DIPSO (3-[N,N-bis(2-Hydroxyethyl)amino]-2-hydroxypropanesulfonic acid), TAPSO (3-[N-tris(Hydroxyethyl)methylamino]-2-hydroxypropanesulfonic acid), HEPPSO (N-[2-Hydroxythyl]piperazine-N'-[2Hydroxypropanesulfonic acid]), POPSO (Piperazine-N,N'-bis[2-hydroxypropanesulfonic acid]), EPPS (N-[2-Hydroxyethyl] piperazine-N'-[3-propanesulfonic acid), TEA (triethanolamine), TRICFNE (N-tris[Hydroxymethyl] methyllycine; N-[2-Hydroxy-1-1-bis(hydroxymethyl)etyyl] glycine), BICINE (N,N-bis[2-Hydroxyethyl]glycine), TAPS (N-tris[Hydroxymethyl]methyl-3-aminopropanesulfonic acid; ([2-Hdroxy-1,1-bis(hydroxymethyl)ethyl]amino)-1-propanesulfonic acid), AMPSO (3-[(1,1-Dimethyl-2-hydroxyethyl)amino]-2-hydroxypropanesulfonic acid), CHES (2-[N-Cyclohexylamino]ethanesulfonic acid), CAPSO (3-[Cyclohexylamino]-2-hydroxy-1-propanesulfonic acid), AMP 2-Amino-2-ethyl-1-propanol, CAPS (3-[cyclohexylamino]-1-propanesulfonic acid), hydrochloric acid, phosphoric acid, lactic. acid, sulfuric acid, nitric acid, chromic acid, boric acid, perchloric acid, potassium hydrogen tartrate, potassium hydrogen phthalate, calcium hydroxide, phosphate, bicarbonate, sodium hydroxide, potassium hydroxide, oxalate or succinate. Other buffers with an effective pK and pH range, and capacity suitable for maintaining the sample-reagent mixture within the required parameters of the assay's reaction mechanism may be added to the above group, however acidic buffers are preferred.

EXAMPLE 6

This example will illustrate in detail the exact method for manufacturing the lateral flow GBL method. Keep in mind this method could be utilized for any general chemistry "test pad" or pads that are currently used or will be used in the art. In the case of DLFH technology, the manufacturing process includes impregnating onto an absorbent, solid carrier (e.g. paper) called in this example, the "test pad", in exactly the same manner as Example 1 with similar constituents. The test pad, once impregnated, is dried, then mounted onto a solid support (nitrocellulose membrane) that is capable of transporting (through lateral flow) liquid to the test pad from the point of application of a test sample. In simpler terms, the device is dipped into a liquid or the liquid sample is placed on the device at the bottom or starting point for the assay. The liquid migrates from the starting application point to the opposite end of the nitrocellulose lateral flow paper, during which the test pad becomes saturated with the sample. The reaction takes place on the test pad and color develops. The developed color is then compared to a color chart with known concentrations of GBL that has the appropriate colors relative to each specific concentration of GBL (s). For example a specific color for 0.0 ug/mL GBL, 50.0 ug/mL, 100.0 ug/mL, etc., for comparison. The results are then recorded. Note, the test pad must be an absorbent (wicking) material that permits migration of sample up the solid absorbent test pad and allows analytes and reactants to interact.

Absorbent material is successively impregnated with the following solutions and dried at 25 degree C.:

Solution I

NAD 0.3 M gamma-butyrolactone dehydrogenase 5 mM

Phosphate buffer 0.01M

NBT (nitro blue tetrazolium) 0.01 mg/L distilled water added to 100 mL total volume of solution pH the solution to a value between 1.0 and 12.5 preferably 8.0 lab notes: Buffer strength is preferably 10 mM or greater

In this example, the lateral flow device is prepared in accordance with the instant invention. The lateral flow device is comprised of a paper carrier matrix (S&S, 593 grade filter paper) impregnated with the compositions of solution 1. The paper is then cut into test pads 5 mm by 5 mm. Note that said concentrations of any of the above constituents can be varied to suit the DLFH lateral flow/ dipstick device format (e.g. dependent upon paper type, and inclusion of semi-permeable membranes or other innovations utilized in dry chemistry technology). The paper is then dried using forced air. The dried impregnated test pad is then placed at approximately 35 mm (in the middle) of a 5 mm wide by 70 mm long nitrocellulose membrane (S&S Fast-Track™ NC) and makes fluid contact with nitrocellulose lateral flow paper. The nitrocellulose membrane is capable of transporting a liquid by capillary action or wicking from one end of the lateral flow device to the other in approximately 60 seconds. In this example, the DLFH has the dimensions of 5 mm wide by 70mm long and can be backed by or in contact with strips of glass fiber filter material (e.g. S&S 30 grade) to aid in controlling the wicking action, or other solid support material can be used.

Again, to completely illustrate the present device the starting point or origin at which the sample is placed on the test device is 5 mm from one end of the strip, and 35 mm from the site of where the test pad is placed in fluid contact with the strip. For simplicity, this example will have the 5 mm by 5 mm impregnated test pad placed on top of the lateral flow paper and thus be in fluid contact with the said paper.

The mechanics of how the present art's LFD and dipstick test pad hybrid may be explained is as follows. The starting point or origin at which the sample is placed on the test device is 5 mm from one end of the strip, and 35 mm from site where the chemically impregnated test pad is in fluid contact with the lateral flow paper. The test pad can be placed on top of the lateral flow paper making fluid contact with the lateral flow paper from the bottom side of the test pad, or the lateral flow paper can touch the paper from the side of the test pad and remain in fluid contact with the test pad. Or the lateral flow paper can rest on top of the edge of test pad or be attached and in fluid contact with the test pad in some other manner. One of the novel advantages in using a hybrid device made of lateral flow material and a dry chemistry test pad is the lack of cross contamination from one pad to the next from excessive fluid, as is inherent in the prior art. For illustration, currently there are available many different types of dry chemistry test strips available, such as the Miles Laboratories, Inc. MULTISTIX®. This device and many other like it has multiple reagents test pads with different chemistries impregnated onto each pad on a single support membrane backing (usually plastic). Because of the relative proximity of these pads to each other on the same device it is easy for cross contamination to occur, causing unreliable results. This is called "runover" (i.e. when a reagent from one pad runs over another adjacent test pad). The present arts eliminates runover. The applicants novel approach to the solution of runover has not been taught prior to the present art and is the result of extensive research and development.

Result interpretation can be explained as follows. If the sample is positive, with a concentration of 50.0 ug/mL GBL or more, the following occurs. A drop of urine (approximately 50 uL) is applied at the starting point or origin of the strip. The urine then migrates to the opposite or terminal end of the strip. As the urine migrates across the lateral flow material (nitrocellulose) and comes into contact with the test pad (filter paper), the urine will saturate the pad and cause a chemical reaction between the impregnated chemicals and GBL in the urine. A blue color will develop on the test pad indicating a positive (greater than 50.0 ug/mL GBL) for the presence of high levels of GBL. This color can then be compared to a color chart showing the different colors from colorless (white background)) to a dark blue depending upon the concentration of the GBL(s), if greater than 50.0 ug/mL. The reaction on the test pad is immediate thus the test results can be observed immediately.

If the sample is negative, with a concentration of less than 50.0 ug/mL of GBL present the following occurs. A drop of urine (approximately 50 uL) is applied at the starting point or origin of the strip. The urine then migrates to the opposite or terminal end of the strip. As the urine migrates across the lateral flow material and comes into contact with the test pad, the urine will saturate the pad and cause a chemical reaction between the impregnated chemicals and GBL. However, this example is for a negative result, thus, no reaction occurs and no color develops, indicating a negative result. This negative result color can then be compared to a color chart showing the different colors from no color developed (negative) to dark blue depending upon the concentration of the GBL, if greater than 50 ug/mL GBL. The reaction on the test pad is immediate thus the test results can be observed immediately.

Changes to the above reagent solution of example 6 can be made and still remain within the scope and function of this invention and will have similar results to examples 4 and 5 above. The indicator(s) and buffer(s) of example 6 can be replaced by all the examples and possible substitutions as illustrated in example 4 and 5.

This brief description of the present art illustrates a completely enabled device that would allow an individual, physician, patient, and/or technician to quickly and easily determine the presence of the GBL in urine, providing a much needed advancement the art of GBL testing.

To briefly explain the present device as taught. The present art includes a device for the detection of GBL in a sample of urine submitted for drugs of abuse testing the steps comprise of preparing a dry chemistry test means by successively impregnating a solid, carrier matrix with reagent solutions containing an indicator and a buffer, and drying the impregnated, solid carrier matrix. Finally, by dipping said dry chemistry test means into urine, one can observe the detectable response in the form of a color developed in the presence or absence of GBL. This present art also illustrates a unique device that will prevent cross contamination (runover) of test pads on the same dipstick, as well as a unique dry chemistry test pad lateral flow device hybrid. These methods can incorporate detectable responses in the visible color range to the human eye or in the visible light spectrum. These methods have a wide sample choice other than urine, and can be replaced by any biological sample including serum, whole blood, cerebral spinal fluid, gastric fluid, hair homogenates, sweat extracts, saliva or other biological fluid and other fluids such as water, beverages (beer, soft drinks, etc.), to include alcohol drinks.

EXAMPLE 7

This is a method for manufacturing a dry chemistry dipstick (test strip) with a solid carrier for the GHB detection of in urine samples submitted for drugs of abuse analysis.

Filter paper is successively impregnated with the following solutions and dried at 25 degree C.:

Solution I

EPPS (N-[2-Hydroxyethyl]piperazine-N'-[3-propanesulfonic acid), buffer 0.97 g distilled water added to 100 mL total volume of solution pH the solution to a value between 1.0 and 12.5 preferably 8.0 lab notes: Buffer strength is preferably 0.01 Molar or greater

Solution 2 esterase 0.01 g/L thymol blue 0.01 g/L distilled water added to make 1000 mL total volume of solution lab notes: esterase needs to be in solution at a concentration 0.001 g/L or greater In this example a dipstick was prepared in accordance with the instant invention. The device comprised a paper carrier or solid matrix incorporated with the composition of solutions 1 and 2 above. Note that the concentrations of any of the following examples can be varied to suit the dipstick device format (dependent upon paper type, or use of semipermeable membrane or other suitable material). This example is carried out using the following procedure. To produce the test means, a piece of Whatman 3 MM filter paper having approximate dimensions of 1 inch by 3 inches was impregnated with solution 1 by immersing the paper into solution 1. The paper was then dried by using forced air not exceeding 25° C. A second piece of Whatman 1 MM filter paper having approximate dimensions of 1 inch by 3 inches was impregnated with solution 2 by immersing the paper into solution 2. The paper was then dried by using forced air not exceeding 25° C. The dried papers are then laminated to each other by the use of a non-reactive (neutral adhesive). The dried, laminated papers are then applied to one side of a piece of double-sided adhesive transfer tape commercially available from 3M Company, St. Paul, Minn. 55144. The laminate is then slit into portions measuring 3 inches by 0.2 inches. One portion is then attached, via the unused adhesive side to a polystyrene sheet measuring about 1.5 inches by 3 inches and the resulting laminate is slit parallel to its short dimension to form test devices comprising a 1.5 inch oblong polystyrene strip carrying a square of the impregnated papers at one end, the other end serving as the handle. When the dipstick thus obtained is dipped into a urine submitted for drugs of abuse testing, and no green color develops then no GHB is present. Conversely, if any concentration of GHB is present in the urine at a 50 ug/mL or greater a green-blue color will develop thus confirming the presence of GHB.

In summary, Example 7 is as follows: the foregoing dry chemistry test strip (dipstick) method for the GHB detection in a sample of urine submitted for drugs of abuse testing comprises the steps of preparing a test means by successively impregnating a solid, carrier matrix with reagent solutions, drying the impregnated, solid test means, then dipping said dried test means into urine, and finally observing any color change in the presence or absence of GHB.

The reaction as illustrated by example 7 can best be understood as follows. When esterase reacts with GHB an acid and alcohol are produced as by-products of the reaction. As more GHB is present, more acid and alcohol is generated by the reaction between GHB and esterase. The detection method for this pathway can take two different directions. The change in pH of the solution can be monitored by the use of a pH indicator or the production of alcohol can be monitored. Example 7 solutions 1 and 2 above illustrate the pH monitoring pathway. Example of the alcohol monitoring pathway will follow.

The following changes to the above reagent solutions will remain within the scope and function of this invention and will have similar results to the example above. The GHB reactive indicator in the solution 1, esterase, could be substituted with one or more of the hydroxybutyrate dehydrogenase, 3-hydroxybutyrate dehydrogenase, 4-hydroxybutyrate dehydrogenase, carboxyl esterase, carboxylic-ester hydrolase, β-hydroxybutyrate dehydrogenase, [R]-3-hydroxybutanoate, NAD (nicotinamide adenine dinucleotide)⁺ oxidoreductase, and α-hydroxybutyrate dehydrogenase, anti-gamma-hydroxybutyrate, alpha-nicotinamide adenine dinucleotide phosphate, beta-nicotinamide adenine dinucleotide phosphate and all analogs of the afore mentioned.

The pH indicator of solution 2, thymol blue could be replaced with one of the following compounds such as bromcresol green, methyl red, cresol red, metanil yellow, m-cresol purple, xylenol blue, thymol blue, tropeolin OO, quinaldine red, α-dinitrophenol, methyl yellow;dimethyl yellow, bromophenol blue, tetrabromophenol blue, bromochlorophenol blue, Congo red, methyl orange, p-ethoxychrysoidine hydrochloride, napthyl red, alizarin sodium sulfonate, bromocresol green, γ-dinitrophenol, methyl red, lacmoid, chlorophenol red, benzoyl auramine G, bromocresol purple, bromophenol red, p-nitrophenol, bromthymol blue, phenol red, p-quinonemono(bis-4-oxyphenylmethide), neutral red, quinoline blue, α-naphtholphthalein, tropeolin OOO; α-napthol orange, ethyl bis(2,4-dinitrophenyl)acetate, di-o-cresolphthalide, phenolphthalein, thymolphthalein, dimethylphenolphthalein, alizarin yellow GG;salicyl yellow, alizarin yellow R, Nile blue, 2,4,6-trinitrophenylmethyl-nitramine, tropeolin O, triphenylrosaniline sulfonic acid (sodium or potassium salt), indigo carmine, nitrobenzene, bromcresol green, bromcresol purple, bromchlorophenol blue, brilliant yellow, brilliant blue R, brilliant cresyl blue ALD, brilliant blue G, brilliant black BN, bromthymol blue, bromphenol red, bromphenol red, bromoxylenol blue, coomasie blue, azolitmin, litmus, pyrogallosulfonphthalein, and pyrogallo red-molybdate.

The EPPS buffer in solution 1, may be substituted with one or more of the following buffers: citrate, borate, borax, sodium tetraborate decahydrate, sodium perchlorate, sodium chlorate, sodium carbonate, (Tris[hydroxymethyl] aminomethane), MES (2-[N-Morpholino]ethanesulfonic acid), BIS-TRIS (bis[2-Hydroxyethyl]iminotris [hydroxymethyl]methane; 2-bis[2-Hydroxyethyl]amino-2-[hydroxymethyl-1,3-propanediol), ADA (N-[2-Acetamidol]-2-iminodiacetic acid; N-[Carbaoylmethyl] iminodiacetc acid), ACES (2-[(2-Amino-2-oxoethyl) aamino]ethanesulfonic acid; N-[2-Acetamido]-2-aminoethanesulfonic acid), PIPES (PiperazineN-N'-bis[2-ethanesulfonic acid)]; 1,4-Piperzinedethanesulfoic acid), MOPSO (3-[N-Morpholinol]-2-hydroxypropanesulfonic acid), BIS-TRIS PROPANE (1,3-bis[tris(Hydroxymethyl) methylamino]propane), BES (N,N-bis[2-Hydroxyethyl]-2-aminoethaesulfonic acid; 2-bis(2-Hydroxyethyl)amino] ethanesulfonic acid), MOPS (3-[N-Morpholino] propanesulfonic acid), TES (N-tris[Hydroxymethyl]methyl-2-aminomethanesulfonic acid; 2[2-Hysroxy-1,1-bis (hydroxymethyl)-ethyl]amino)ethanesulfonic acid), DIPSO (3-[N,N-bis(2-Hydroxyethyl)amino]-2-hydroxy- propanesulfonic acid), TAPSO (3-[N-tris(Hydroxyethyl) methylamino]-2-hydroxypropanesulfonic acid), HEPPSO (N-[2-Hydroxythyl]piperazine-N'-[2Hydroxypropanesulfonic acid]), POPSO (Piperazine-N,N'-bis[2-hydroxypropanesulfonic acid]), TEA (triethanolamine), TRICINE (N-tris[Hydroxymethyl]methyllycine; N-[2-Hydroxy-1-1-bis(hydroxymethyl)etyyl]glycine), BICINE (N,N-bis[2-Hydroxyethyl]glycine), TAPS (N-tris [Hydroxymethyl]methyl-3-aminopropanesulfonic acid; ([2-Hdroxy-1,1-bis(hydroxymethyl)ethyl]amino)-1-propanesulfonic acid), AMPSO (3-[(1,1-Dimethyl-2-hydroxyethyl)amino]-2-hydroxypropanesulfonic acid), CHES (2-[N-Cyclohexylamino]ethanesulfonic acid), CAPSO (3-[Cyclohexylamino]-2-hydroxy-1-propanesulfonic acid), AMP 2-Amino-2-ethyl-1-propanol, CAPS (3-[cyclohexylamino]-1-propanesulfonic acid), Hepes, hydrochloric acid, phosphoric acid, lactic acid, sulfuric acid, nitric acid, chromic acid, boric acid, perchloric acid, potassium hydrogen tartrate, potassium hydrogen phthalate, calcium hydroxide, phosphate, bicarbonate, sodium hydroxide, potassium hydroxide, oxalate or succinate. Other buffers with an effective pK and pH range, and capacity suitable for maintaining the sample-reagent mixture within the required parameters of the assay's reaction mechanism may be added to the above group.

Now, if in example 7, solution 2 were formulated as follows, then the by product of the reaction (GHB and esterase) alcohol is acted upon by the alcohol oxidase. Solution 2 in this example is then used in the same manner as solution 2 previously in example 7 and applied to the matrix as previously illustrated.

Solution 2 esterase 0.01 g/L alcohol oxidase 0.01 mM

ABTS (2,2'-azinobis(3-ethylbenzothiazoline-6-sulfonic acid)) 0.01% distilled water added to make 1000 mL total volume of solution lab notes: alcohol oxidase needs to be in solution at a concentration 0.001 mM or greater In this reaction the alochol oxidase is specific for methanol and not ethanol (which is the alcohol found in beverages). Methanol would be poisonous.

Therefore, in this example a dipstick was prepared in accordance with the instant invention. The device comprised a paper carrier or solid matrix incorporated with the composition of solutions 1 of example 7 above and the second example of solution 2 above containing the alcohol oxidase. Note that the concentrations of any of the following examples can be varied to suit the dipstick device format (dependent upon paper type, or use of semi-permeable membrane or other suitable material). This example is carried out using the following procedure. To produce the test means, a piece of Whatman 3 MM filter paper having approximate dimensions of 1 inch by 3 inches was impregnated with solution 1 by immersing the paper into solution 1. The paper was then dried by using forced air not exceeding 25° C. A second piece of Whatman 1 MM filter paper having approximate dimensions of 1 inch by 3 inches was impregnated with solution 2 by immersing the paper into solution 2. The paper was then dried by using forced air not exceeding 25° C. The dried papers are then laminated to each other by the use of a non-reactive (neutral adhesive). The dried, laminated papers are then applied to one side of a piece of double-sided adhesive transfer tape commercially available from 3M Company, St. Paul, Minn. 55144. The laminate is then slit into portions measuring 3 inches by 0.2 inches. One portion is then attached, via the unused adhesive side to a polystyrene sheet measuring about 1.5 inches by 3 inches and the resulting laminate is slit parallel to its short dimension to form test devices comprising a 1.5 inch oblong polystyrene strip carrying a square of the impregnated papers at one end, the other end serving as the handle. When the dipstick thus obtained is dipped into a urine submitted for drugs of abuse testing, and no uniform green-blue color develops then no GHB is present. Conversely, if any concentration of GHB is present in the urine at a 50 ug/mL or greater a blue-green color will develop thus confirmning the presence of GHB.

In summary, Example 7 is as follows: the foregoing dry chemistry test strip (dipstick) method for the GHB detection in a sample of urine submitted for drugs of abuse testing comprises the steps of preparing a test means by successively impregnating a solid, carrier matrix with reagent solutions, drying the impregnated, solid test means, then dipping said dried test means into urine, and finally observing any color change in the presence or absence of GHB.

The reaction as illustrated by example 7 can best be understood as follows. When esterase reacts with GHB an acid and alcohol are produced as by-products of the reaction. As more GHB is present, more acid and alcohol is generated by the reaction between GHB and esterase. The detection method for this pathway can take two different directions. The change in pH of the solution can be monitored by the use of a pH indicator or the production of alcohol can be monitored. Example 7 solution 1 and solution 2 (containing alcohol oxidase) illustrates using the alcohol monitoring pathway. Alcohol oxidase in this example will produce as a by product of the reaction, hydrogen peroxide.

The following changes to the above reagent solutions will remain within the scope and function of this invention and will have similar results to the example above. The GHB reactive indicator in the solution 1, esterase, could be substituted with one or more of the hydroxybutyrate dehydrogenase, 3-hydroxybutyrate dehydrogenase, 4-hydroxybutyrate dehydrogenase, carboxyl esterase, carboxylic-ester hydrolase, β-hydroxybutyrate dehydrogenase, [R]-3-hydroxybutanoate, NAD (nicotinamide adenine dinucleotide)$^+$ oxidoreductase, and x-hydroxybutyrate dehydrogenase, anti-gamma-hydroxybutyrate, alpha-nicotinamide adenine dinucleotide phosphate, beta-nicotinamide adenine dinucleotide phosphate and all analogs of the afore mentioned.

The alcohol reactive enzyme of solution 2, alcohol oxidase could be replaced with one or more of the following compounds such as alcohol dehydrogenase, NAD, NADP, or any other enzyme or antibody reactive to the production of alcohol as a result of the interaction of esterase and GHB.

The EPPS buffer in solution 1, may be substituted with one or more of the following buffers: citrate, borate, borax, sodium tetraborate decahydrate, sodium perchlorate, sodium chlorate, sodium carbonate, (Tris[hydroxymethyl] aminomethane), MES (2-[N-Morpholino]ethanesulfonic acid), BIS-TRIS (bis[2-Hydroxyethyl]iminotris [hydroxymethyl]methane; 2-bis[2-Hydroxyethyl]amino-2-[hydroxymethyl-1,3-propanediol), ADA (N-[2-Acetamidol]-2-iminodiacetic acid; N-[Carbaoylmethyl] iminodiacetc acid), ACES (2-[(2-Amino-2-oxoethyl)amino] ethanesulfonic acid; N-[2-Acetamido]-2-aminoethanesulfonic acid), PIPES (PiperazineN-N'-bis[2-ethanesulfonic acid)]; 1,4-Piperzinedethanesulfoic acid), MOPSO (3-[N-Morpholinol]-2-hydroxypropanesulfonic acid), BIS-TRIS PROPANE (1,3-bis[tris(Hydroxymethyl) methylamino]propane), BES (N,N-bis[2-Hydroxyethyl]-2-aminoethaesulfonic acid; 2-bis(2-Hydroxyethyl)amino] ethanesulfonic acid), MOPS (3-[N-Morpholino] propanesulfonic acid), TES (N-tris[Hydroxymethyl]methyl-2-aminomethanesulfonic acid; 2[2-Hysroxy-1,1-bis (hydroxymethyl)-ethyl]amino)ethanesulfonic acid), DIPSO (3-[N,N-bis(2-Hydroxyethyl)amino]-2-hydroxypropane-sulfonic acid), TAPSO (3-[N-tris(Hydroxyethyl) methylamino]-2-hydroxypropanesulfonic acid), HEPPSO (N-[2-Hydroxythyl]piperazine-N'-[2Hydroxypropane-sulfonic acid]), POPSO (Piperazine-N,N'-bis[2-hydroxypropanesulfonic acid]), TEA (triethanolamine), TRICINE (N-tris[Hydroxymethyl]methyllycine; N-[2-Hydroxy-1-1-bis(hydroxymethyl)etyyl]glycine), BICINE (N,N-bis[2-Hydroxyethyl]glycine), TAPS (N-tris [Hydroxymethyl]methyl-3-aminopropanesulfonic acid; ([2-Hdroxy-1,1-bis(hydroxymethyl)ethyl]amino)-1- propanesulfonic acid), AMPSO (3-[(1,1-Dimethyl-2-hydroxyethyl)amino]-2-hydroxypropanesulfonic acid), CHES (2-[N-Cyclohexylamino]ethanesulfonic acid), CAPSO (3-[Cyclohexylamino]-2-hydroxy-1-propanesulfonic acid), AMP 2-Amino-2-ethyl-1-propanol, CAPS (3-[cyclohexylarnino]-1-propanesulfonic acid), Hepes, hydrochloric acid, phosphoric acid, lactic acid, sulfuric acid, nitric acid, chromic acid, boric acid, perchloric acid, potassium hydrogen tartrate, potassium hydrogen phthalate, calcium hydroxide, phosphate, bicarbonate, sodium hydroxide, potassium hydroxide, oxalate or succinate. Other buffers with an effective pK and pH range, and capacity suitable for maintaining the sample-reagent mixture within the required parameters of the assay's reaction mechanism may be added to the above group.

The indicator used in solution 2, ABTS (2,2'-azinobis(3-ethylbenzothiazoline-6-sulfonic acid)) is an oxygen acceptor and is sensitive to the presence of hydrogen peroxide and can be substituted with one or more of the following: 4-aminoantipyrine (4AAP), tetramethylbenzidine (TMB), o-phenylenediamine (OPD), o-dianisidine, 5-aminosalicylic acid (SAS), 3,3'-diaminobenzidine (DAB), 3-amino-9-ethylcarbazole (AEC), 4-chloro-1-napthol (4C1N), or other suitable compound that produces an observable color for the peroxidase/peroxide reaction. Other such compounds may include, AEC (3-Amino-9-ethyl carbazole), 2-5, dimethyl-2,5-dihydroperoxyhexane, Bis{4-[N-(3'-sulfo-n-propyl)-N-n-ethyl]amino-2,6-dimethylphenyl}methane (Bis-MAPS), N-Ethyl-N-(2-hydroxy-3-sulfopropyl)-3-methoxyaniline (ADOS), N-Ethyl-N-(3-sulfopropyl)-3-methoxyaniline (ADPS), N-Ethyl-N-(2-hydroxy-3-sulfopropyl)aniline (ALOS), N-Ethyl-N-(3-sulfopropyl)-3,5-dimethylaniline (MAPS), N-Ethyl-N-(2-hydroxy-3-sulfopropyl)-3-methylaniline (TOOS), N-Ethyl-N-(3-sulfopropyl)-3-methylaniline (TOPS), N-(3-sulfopropyl)aniline (HALPS), N-Ethyl-N-(2-hydroxy-3-sulfopropyl)-3,5-dimethoxyaniline (DAOS), N-Ethyl-N-(3-sulfopropyl)-3,5-dimethoxyaniline (DAPS), N-Ethyl-N-(3-sulfopropyl)aniline (ALPS), N-(2-hydroxy-3-sulfopropyl)-3,5-dimethoxyaniline (HDAOS), N-(3-sulfopropyl)-3,5-dimethoxyaniline (HDAPS), N-Ethyl-N-(2-hydroxy-3-sulfopropyl)-3,5-dimethylaniline (MAO), N,N-Bis(4-sulfobutyl)-3,5-dimethylaniline (MADB), and pyrogallol. Also, 4-aminoantipyrine can be paired with a number of compounds to create a violet to violet-blue color complex in the presence of the peroxide/peroxidase reaction. These compounds include 2,4-Dichlorophenol, N,N-Diethyl-m-toluidine, p-Hydroxybenzene Sulfonate, N,N-Dimethylaniline, 3,5-Dichloro-2-Hydroxybenzenesulfonate, 2,4,6-tribromo-3-hydroxybenzoic acid, Sodium N-Ethyl-N-(3-Sulfopropyl)-m-Anisidine, hydroxybenzoic acid, 4-hydroxybenzoic acid, N-Ethyl-N-(2-hydroxy-3-Sulfopropyl)-m-toluidine, AEC (3-Amino-9-ethyl carbazole), 2-5, dimethyl-2,5-dihydroperoxyhexane, Bis{4-[N-(3'-sulfo-n-propyl)-N-n-ethyl]amino-2,6-dimethylphenyl}methane (Bis-MAPS), N-Ethyl-N-(2-hydroxy-3-sulfopropyl)-3-methoxyaniline (ADOS), N-Ethyl-N-(3-sulfopropyl)-3-methoxyaniline (ADPS), N-Ethyl-N-(2-hydroxy-3-sulfopropyl)aniline (ALOS), N-Ethyl-N-(3-sulfopropyl)-3,5-dimethylaniline (MAPS), N-Ethyl-N-(2-hydroxy-3-sulfopropyl)-3-rmethylaniline (TOOS), N-Ethyl-N-(3-sulfopropyl)-3-methylaniline (TOPS), N-(3-sulfopropyl)aniline (HALPS), N-Ethyl-N-(2-hydroxy-3-sulfopropyl)-3,5-dimethoxy-aniline (DAOS), N-Ethyl-N-(3-sulfopropyl)-3,5-dimethoxyaniline (DAPS), N-Ethyl-N-(3-sulfopropyl)aniline (ALPS), N-(2-hydroxy-3-sulfopropyl)-3,5-dimethoxyaniline (HDAPS), N-Ethyl-N-(2-hydroxy-3-sulfopropyl)-3,5-dimethylaniline (MAO), N,N-Bis(4-sulfobutyl)-3,5-dimethylaniline (MADB), and pyrogallol. Another indicator pair that may be utilized consists of 3-Methyl-2-benzothiazolinonehydrazone and Dimethylaniline.

EXAMPLE 8

This is a method for manufacturing a liquid, carrier-free reagent for the adulteration detection of GHB in samples submitted for drugs of abuse analysis.

Prepare a Solution Containing:

Solution I (R1)

phosphate buffer 1.0 M esterase distilled water added to make 1000 mL total volume of solution lab notes: a) pH the solution to a value between 1.0 and 12.5 preferably 8.0 b) Buffer strength is preferably 0.01 Molar or greater c) NBT needs to be in solution at a concentration 0.001 mg/L or greater Solution II (R2)

phosphoric acid 1.0 M sodium dichromate 10.0 mg/dL lab notes: a) pH final solution to a value of 2.0 (range of 1.0 14.0)

GHB Calibrator Formulations

Zero (0) calibrator:

1 liter of 0.2 micron filtered normal human urine with no adulterants or drugs present, and 0.01% sodium azide.*

50 uglmL calibrator:

50 ug/mL GHB 0.01 M Sodium Borate 100 mL of 0.2 micron filtered normal human urine with no adulterants or drugs present* pH the solution to a value between 3.0 and 11.0 preferably 9.0.

lab notes:* Human urine can be substituted with distilled water, synthetic urine or other suitable solvent. The bacterial inhibitor sodium azide could be replaced with chloroamphenicol or other suitable bacterial inhibitors that would inhibit the growth of bacteria.

The reagent system of the instant invention (liquid reagent) is intended for use on any automatic chemistry analyzers with open channel capability including Olympus series, Hitachi 700 series, Beckmans and many others. The reagent as outlined in Example 2 is used in the following manner: the one component of the reagent composition (R-1) is placed in the reagent compartment of the analyzer; samples, calibrators, and controls are aliquoted into sample cups which are then placed on the analyzer. An aliquot of 5 uL of each specimen is then pipetted into a single, discrete cuvette followed by the addition of 150 uL of the first reagent, R-1, and mixed; Then the second reagent, R-2 is added to the cuvettes for each sample (urine, unknown, calibrator, standard, quality control, etc.,), and mixed; then A first spectrophotometer reading is then taken followed by a second after a specified incubation period (i.e. one minute for this example) at the specified wavelength (between 340 and 800 nm). The spectrophotometer readings are then recorded. In this instance the assay is read at 600 nm. The absorbance of samples, and controls are printed and then compared to the calibrator's absorbance. The quantitative value for GHB concentration is then calculated. Any concentration of GHB greater than 50.0 ug/mL is considered positive for the presence of GHB.

Please note if the present art is not used as illustrated that very significant increase in the cost of analysis, because a GC-MS assay must then be performed to verify the presence of GHB. The GC-MS analysis costs 100 times as much as the screen ($100 vs $1). Every additional unnecessary GC-MS performed drives up the overall cost of drug testing. Eliminating these additional, unnecessary assays will save millions of dollars per year.

Specifications for running urine samples vary from instrument to instrument. Listed below is an example of parameters for the Hitachi 700 series analyzer. The settings are intended as guidelines, and are set forth with the understanding that all those skilled in the art would recognize that such parameters will vary from instrument to instrument. The suggested specifications for the Hitachi 700 series are as follows:

| Parameter settings for the Hitachi 700 series | |
|---|---|
| Test: | [GHB] |
| Assay code: | [1 POINT] [50] - [0] |
| Sample volume: | [5] [5] |
| R1 volume | [150] [100] [NO] |
| R2 volume | [150] [100] [NO] |
| Wavelength | [0] [600] |
| Calib. Method: | [Linear] [0] [0] |
| Std. (1) Conc.-POS: | [0.0] *-[1]* assigned calibrator value |
| Std. (2) Conc.-POS: | [50.0] -[2] assigned calibrator value |
| Std. (3) Conc.-POS: | [ ] - [ ] |
| Std. (4) Conc.-POS: | [ ] - [ ] |
| Std. (5) Conc.-POS: | [ ] - [ ] |
| Std. (6) Conc.-POS: | [ ] - [ ] |
| SD Limit: | [999] |
| Duplicate Limit: | [32000] |
| Sensitivity Limit: | [0] |
| ABS. Limit (INC/DEC): | [32000] [INCREASE] |
| Prozone Limit: | [0] [lower] |
| Expected Value: | [0.0] - [1.0] |
| Tech. Limit: | [0] - [1000] |
| Instrument Factor | [1.0] |

Note: this assay is to be performed at the same temperature used for the DAU testing, usually 37 degrees Centigrade. However, this can vary without affecting the assay. The temperature could be between refrigerated to 45 degrees Centigrade.

Thus as described above, an unknown urine submitted for drugs of anaylsis for GHB will produce a value of less than the 0.0 ug/mL if no GHB is present. Conversely, if the sample has a concentration of greater than 50.0 ug/mL than the sample is positive for GHB.

To summarize more specifically Example 8, the automated method for the detection of adulteration of an unknown sample of urine submitted for drugs of abuse testing comprising the steps of placing aliquots of an unknown urine (or other biological sample i.e. serum, whole blood, cerebral spinal fluid, gastric fluid, hair homogenates, sweat extracts, saliva or other biological fluid and other fluids such as beverages, water, etc.) and calibrator to be tested in automated analyzer sampling cups, placing the cups in a sampling tray within an automated analyzer, transferring the aliquots of sample and calibrator to cuvettes mounted within the automated analyzer, injecting a first reagent composition (R-1) comprising an GHB reactive compound and buffer in an aqueous medium into the cuvettes, mixing sample and reagent, then second reagent composition (R-2) comprising the alcohol indicator is an aqueous medium into the cuvettes and again the mixing of sample and reagents occurs, and reading absorbance values of reaction mixture composed of reagents and test samples (said test samples include urine specimens, controls, and calibrator) at specified intervals, in accordance with a preprogrammed code introduced into the automated analyzer, at a preprogrammed monochromatically specified wavelength, and comparing absorbance of the first reagent composition plus the unknown samples with that of the first reagent composition plus the calibrator containing a zero reference point (normal urinary matrix), and thereby determining quantitatively the presence or absence of GHB.

The following changes to the above reagent solutions will remain within the scope and function of this invention and will have similar results to the example above. The indicator in the solution 1, GHB, which is the indicator reactive compound (reactive in this sense means that esterase is sensitive (reactive) the presence of GHB and will react with GHB during which alcohol and acid is produced) in solution 1 is esterase, which could be substituted with one or more of the following compounds including hydroxybutyrate dehydrogenase 3-hydroxybutyrate dehydrogenase, 4-hydroxybutyrate dehydrogenase, carboxyl esterase, carboxylic-ester hydrolase, β-hydroxybutyrate dehydrogenase, [R]-3-hydroxybutanoate, NAD (nicotinamide adenine dinucleotide)$^+$ oxidoreductase, and α-hydroxybutyrate dehydrogenase, anti-gamma-hydroxybutyrate, alpha-nicotinamide adenine dinucleotide phosphate, beta-nicotinamide adenine dinucleotide phosphate and all analogs of the afore mentioned.

The phosphate buffer in solution 1 and phosphoric acid buffer of solution, may be substituted with one or more of the following buffers: citrate, borate, borax, sodium tetraborate decahydrate, sodium perchlorate, sodium chlorate, sodium carbonate, MES (2-[N-Morpholino]ethanesulfonic acid), BIS-TRIS (bis[2-Hydroxyethyl]iminotris [hydroxymethyl]methane; 2-bis[2-Hydroxyethyl]amino-2-[hydroxymethyl-1,3-propanediol), ADA (N-[2-Acetamidol]-2-iminodiacetic acid; N-[Carbaoylmethyl] iminodiacetc acid), ACES (2-[(2-Amino-2-oxoethyl)amino] ethanesulfonic acid; N-[2-Acetamido]-2-aminoethanesulfonic acid), PIPES (PiperazineN-N'-bis[2-ethanesulfonic acid)]; 1,4-Piperzinedethanesulfoic acid), MOPSO (3-[N-Morpholinol]-2-hydroxypropanesulfonic acid), BIS-TRIS PROPANE (1,3-bis[tris(Hydroxymethyl) methylamino]propane), TRIS, BES (N,N-bis[2-Hydroxyethyl]-2-aminoethaesulfonic acid; 2-bis(2-Hydroxyethyl)amino]ethanesulfonic acid), MOPS (3-[N-Morpholino]propanesulfonic acid), TES (N-tris [Hydroxymethyl]methyl-2-aminomethanesulfonic acid; 2[2-Hysroxy-1,1-bis(hydroxymethyl)-ethyl]amino) ethanesulfonic acid), HEPES (N-[2-Hydroxyethyl] piperazine-N'-[2-ethanesulfonic acid]), DIPSO (3-[N,N-bis (2-Hydroxyethyl)amino]-2-hydroxypropanesulfonic acid), TAPSO (3-[N-tris(Hydroxyethyl)methylamino]-2-hydroxypropanesulfonic acid), HEPPSO (3-[2-Hydroxythyl]piperazine-N'-[2Hydroxypropanesulfonic acid]), POPSO (Piperazine-N,N'-bis[2-hydroxypropanesulfonic acid]), EPPS (N-[2-Hydroxyethyl] piperazine-N'-[3-propanesulfonic acid), TEA (triethanolamine), TRICINE (N-tris[Hydroxymethyl] methyllycine; N-[2-Hydroxy-1-1-bis(hydroxymethyl)etyyl] glycine), BICINE (N,N-bis[2-Hydroxyethyl]glycine), TAPS (N-tris[Hydroxymethyl]methyl-3-aminopropanesulfonic acid; ([2-Hdroxy-1,1-bis(hydroxymethyl)ethyl]amino)-1-propanesulfonic acid), AMPSO (3-[(1,1-Dimethyl-2-hydroxyethyl)amino]-2-hydroxypropanesulfonic acid), CHES (2-[N-Cyclohexylamino]ethanesulfonic acid), CAPSO (3-[Cyclohexylamino]-2-hydroxy-1- propanesulfonic acid), AMP 2-Amino-2-ethyl-1-propanol, CAPS (3-[cyclohexylamino]-1-propanesulfonic acid), hydrochloric acid, phosphoric acid, lactic acid, sulfuric acid, nitric acid, chromic acid, boric acid, perchloric acid, potassium hydrogen tartrate, potassium hydrogen phthalate, calcium hydroxide, phosphate, bicarbonate, sodium hydroxide, potassium hydroxide, oxalate or succinate. Other buffers with an effective pK and pH range, and capacity suitable for maintaining the sample-reagent mixture within the required parameters of the assay's reaction mechanism may be added to the above group, however acidic buffers are preferred.

The indicator of the presence of alcohol in solution sodium dichromate may be replaced with one or more of the following: sulfuric acid, sodium salicylate, sodium hydroxide, iodine, potassium permanganate or other alcohol reactive indicators or analogs of the afore mentioned.

EXAMPLE 9

The following procedure is a method for manufacturing a dry chemistry test strip (DCD), for the determination of GHB in a test sample.

Filter paper is impregnated with the following solutions and dried at 25 degree C.:

Solution 1

30.2 G PIPES (1,4-Piperazinediethanesulfonic acid)

0.05 Units/mL beta-Galactosidase/anti-GHB (enzyme conjugated to the anti-GHB)

add to 900 mL D.I. water, mix, adjust pH to 6.8, Q.S. to 1000 mL

Solution 2

0.01 M 5-bromo-6-chloro-3-indoxyl-beta-D-galactopyranoside (Magenta-beta-D-Gal)

1 mL (0.1%) DMSO dissolve in 900.0 mL distilled water, mix, and Q.S. to 1000 mL.

In this example, a dipstick is prepared in accordance with the instant invention as described in Example 1, however. Solution 1 and 2 are both incorporated into the test device by immersing the test paper into solution 1; drying the paper; then immersing the test paper into solution 2; the paper is then dried by using forced air not exceeding 60 degrees C. If a two-part test pad "sandwich" is used, the pad with solution #1 must be on top and the pad with solution 2 is on the bottom. The dipstick thus obtained will produce a magenta color when exposed to GHB at a concentration of 50 ug/mL or greater. In fact, the intensity of the magenta color is proportional to the concentration of the GHB, present in the sample. This test device, therefore, effectively identifies the presence of GHB in urine by the measurement of the GHB in the urine sample used for illustrative purposes in this example.

To summarize Example 7 more specifically, the foregoing dry chemistry test strip (DCD) method to measure the GHB concentration in a urine sample (or other matrices) for the determination of presence of absence of GHB using said sample, the method comprising the steps of preparing a test means by successively impregnating an absorbent carrier matrix with reagent solutions, drying said test means, dipping completed test means into test sample, and determining the quantity of GHB present in said test sample by comparing the relative intensity of the color (magenta) produced by the reaction to a color chart with color blocks referenced to specific concentrations of GHB.

Changes to the foregoing solutions could be made and still have similar results. In addition, changes to the foregoing solutions or use of the identical solutions as illustrated could be used in an automated analyzer and produce the same results. The foregoing solutions could be combined together, or reduced to include only 1. The concentrations of said constituents may also be changed and still remain within the scope of the invention. The buffer may be replaced with any one or more of those constituents enumerated in Example 1.

The indicator substrate complex in the solution 5-bromo-6-chloro-3-indoxyl-beta-D-galacatopyranoside, could be substituted with one or more of the following: 4-Aminophenyl-beta-D-galactopyranoside, 3-indoxyl-beta-D-galactopyranoside (blue), 5-Bromo-4-chloro-3-indoxyl-beta-D-galactopyranoside (blue), 5-Bromo-3-indoxyl-beta-D-galactopyranoside (blue), 6-chloro-3-indoxyl-beta-D-galactopyranoside (salmon), 6-Fluoro-3-indoxyl-beta-D-galactopyranoside, 8-Hydroxyquinoline-beta-D-galactopyrano-side, 5-Iodo-3-indoxyl-beta-D-galactopyranoside (purple), N-Methylindoxyl-beta-D-galactopyranoside, 2-Nitrophenyl-beta-D-galactopyranoside, 4-Nitrophenyl-beta-D-galactopyranoside, Naphthol AS-BI-beta-D-galactopyranoside, and 2-Naphthyl-beta-D-galactopyranoside (yellow). Fluorescent substrates may also be utilized including 4-Methylumbelliferyl-beta-D-glucuronic acid. The colors noted in the parentheses are those produced in the reaction described above. The indicator substrate used in these examples must be matched to the conformation of the galactosidase used (i.e. alpha or beta, and dextrorotary (D) or levorotary (L)). For example, beta-D-Galactosidase should be matched with the indicator/substrate Iodo-3-indoxyl-beta-D-galactopyranoside; conversely, alpha-L-Galactosidase would be matched with Iodo-3-indoxyl-alpha-L-galactopyranoside. Note that some cross-reactivity does occur between stereo-isomers and, therefore, it is possible to substitute these compounds where appropriate.

Substitution of the beta-Galactosidase with another enzyme would necessitate a change of substrate indicator complex. If another glycosidase was selected, it would have to be matched to the appropriate substrate (e.g. beta-Cellobiosidase and a cellobioside). Examples of substrates for beta-D-Cellobiosidase include 5-Bromo-4-chloro-3-indoxyl-beta-D-cellobioside, 5-Bromo-6-chloro-3-indoxyl-beta-D-cellobioside, 4-Nitrophenyl-beta-D-cellobioside, 1-Naphthyl-cellobioside, and the fluorescent indicator, 4-Methylumbelliferyl-beta-D-cellobioside.

Other glycosidases which may be substituted for Galactosidase and Cellobiosidase include the alpha and beta, and D and L conformnations of the following enzymes: Arabinosidase, Fucosidase, Galactosaminidase, Glucosaminidase, Glucosidase, Glucuronidase, Lactosidase, Maltosidase, Mannosidase, and Xylosidase. Their corresponding substrates, Arabinopyranoside, Fucopyranoside, Galactosaminide, Glucosaminide, Glucopyranoside, Glucuronic acid, Lactopyranoside, Maltopyranoside, Mannopyranoside, and Xylopyranoside may be bound to each of the following color indicator groups: 5-Bromo-4-chloro-3-indoxyl, 5-Bromo-6-chloro-3-indoxyl, 6-chloro-3-indoxyl, 5-Bromo-3-indoxyl, 5-Iodo-3-indoxyl, 3-indoxyl, 2-(6-Bromonaphthyl), 6-Fluoro-3-indoxyl 2-Nitrophenyl, 4-Nitrophenyl, 1-Naphthyl, Naphthyl AS-BI, 2-Nitrophenyl-N-acetyl, 4-Nitrophenyl-N-acetyl, and 4-Methylumbelliferyl moieties.

The glycosidase enzyme conjugated to the anti-GHB in the example above can also be replaced by other types of enzymes whose substrates are compatible with the indicator groups listed above. These include esterases (e.g. Carboxyl esterase, and Cholesterol esterase), sulfatases (e.g. Aryl sufatase), and phosphatases (e.g. Alkaline phosphatase). These enzymes can utilize the indicator groups delineated above when conjugated to the corresponding substrate. For example, Carboxyl esterase and 6-chloro-3-indoxyl butyrate, and Aryl sulfatase and 5-bromo-4-chloro-3-indoxyl sulfate, and Alkaline phosphatase and 2-naphthyl phosphate form enzyme-substrate pairs.

Other enzymes may be conjugated to the anti-GHB, and therefore substituted for the species described above. This group now listed, however, must utilize a substrate that is distinct and separate from the indicator. This enzyme group may include any dehydrogenase, oxidase, hydroxylase, or oxidoreductase. Each grouping will utilize a specific indicator or group of indicators. The dehydrogenases and hydroxylases will utilize a co-enzyme, a color indicator and an electron carrier such as a-NAD (a-Nicotinamide adenine dinucleotide) or NADP, however these electron carrier/acceptors can be replaced by the alpha or beta isomers of any one of the following substitutes: nicotinamide adenine dinucleotide, nicotinamide adenine dinucleotide 3'-phosphate, nicotinamide adenine dinucleotide phosphate, triphosphopyridine, nicotinamide 1-N1-ethenoadenine dinucleotide phosphate, nicotinamide hypoxanthine dinucleotide, nicotinamide hypoxanthine dinucleotide phosphate, nicotinamide mononucleotide, nicotinamide N1-propylsulfonate, nicotinamide ribose monophosphate, or other analogs of NAD or NADP.

Some dehydrogenases and hydroxylases and their substrate pairs which can be used include Formaldehyde dehydrogenase and Formaldehyde, Fructose dehydrogenase and Fructose, Glucose-6-phosphate dehydrogenase and Glucose-6-phosphate, Glucose dehydrogenase and Glucose, Glutamate dehydrogenlase and Glutamate, Glycerol dehydrogenase and Glycerol, Glycerol-3-phosphate dehydrogenase and Glycerol-3-phosphate, Hydroxybutyrate dehydrogenase and Hydroxybutyrate, Hydroxybenzoate hydroxylase and 4-Hydroxybenzoate, Lactate dehydrogenase and Lactate, Leucine dehydrogenase and Leucine, Malate dehydrogenase and Malate, Mannitol dehydrogenase and Mannitol, or any other dehydrogenase or hydroxylase.

The use of oxidases to replace the glycosidase also requires a separate indicator, and peroxidase. Some oxidases and their substrate pair which can be used include Acyl-CoA oxidase and Acyl-CoA, Alcohol oxidase and Ethanol, Ascorbate oxidase and Ascorbate, Cholesterol oxidase and Cholesterol, Choline oxidase and Choline, Glucose oxidase and Glucose, Glycerophosphate oxidase and Glycerophosphate, Xanthine oxidase and Xanthine, Uricase and Uric acid, or any other oxidase.

A few color indicators that can be utilized with peroxidase include pyrogallol, ABTS (2,2'-Azinobis(3-ethylbenzthiazoline) sulfonic acid), 3,3',5,5'-Tetramethylbenzidine, ortho-Dianisidine, 3,3'-Diaminibenzidine, AEC (3-Amino-9-ethyl carbazole), 2-5, dimethyl-2,5-dihydroperoxyhexane, Bis{4-[N-(3'-sulfo-n-propyl)-N-n-ethyl]amino-2,6-dimethylphenyl}methane (Bis-MAPS), N-Ethyl-N-(2-hydroxy-3-sulfopropyl)-3-methoxyaniline (ADOS), N-Ethyl-N-(3-sulfopropyl)-3-methoxyaniline (ADPS), N-Ethyl-N-(2-hydroxy-3-sulfopropyl)aniline (ALOS), N-Ethyl-N-(3-sulfopropyl)-3,5-dimethylaniline (MAPS), N-Ethyl-N-(2-hydroxy-3-sulfopropyl)-3-methylaniline (TOOS), N-Ethyl-N-(3-sulfopropyl)-3-methylaniline (TOPS), N-(3-sulfopropyl) aniline (HALPS), N-Ethyl-N-(2-hydroxy-3-sulfopropyl)-3,5-dimethoxy-aniline (DAOS), N-Ethyl-N-(3-sulfopropyl)-3,5-dimethoxyaniline (DAPS), N-Ethyl-N-(3-sulfopropyl) aniline (ALPS), N-(2-hydroxy-3-sulfopropyl)-3,5-dimethoxyaniline (HDAOS), N-(3-sulfopropyl)-3,5-dimethoxyaniline (HDAPS), N-Ethyl-N-(2-hydroxy-3-sulfopropyl)-3,5-dimethylaniline (MAO), and N,N-Bis(4-sulfobutyl)-3,5-dimethylaniline (MADB). An indicator pair may also be used. One such pair is 3-Methyl-2-benzothiazolinonehydrazone and Dimethylaniline. Another pair combines 4-aminoantipyrine with a number of compounds to create a violet to violet-blue color complex in the presence of the peroxide/peroxidase reaction. These compounds include phenol, 2,4-Dichlorophenol, N,N-Diethyl-m-toluidine, p-Hydroxybenzene Sulfonate, N,N-Dimethylaniline, 3,5-Dichloro-2-Hydroxybenzenesulfonate, Sodium N-Ethyl-N-(3-Sulfopropyl)-m-Anisidine, and N-Ethyl-N-(2-hydroxy-3-Sulfopropyl)-m-toluidine. An example of this assay procedure would substitute glucose oxidase for galactosidase in the antibody-enzyme conjugate in R-1; the R-2 would then contain glucose as the substrate and ABTS (reduced) as the indicator. The R-2 would also contain peroxidase, because the product of the reaction between glucose oxidase and glucose yields peroxide. The peroxidase oxidizes any peroxide thus produced, thereby releasing an oxygen atom; this oxygen, in turn, reacts with ABTS, and converts it from the colorless, reduced form to its blue, oxidized form. The intensity of the blue color produced is proportional to the GHB concentration present in the specimen. Clearly, peroxidase may be conjugated to the antibody, and the indicators noted above used with it and its substrate, peroxide.

The use of oxireductases to replace glycosidase also requires a separate indicator including NADPH oxidoreductase and NADPH, or any oxidoreductase. The NADPH oxireductase reduces the NADPH in the presence of Flavin mononucleotide (FMN). This reaction may be observed visually by utilizing the same color indicators as delineated for the dehydrogenases, or measured spectrophotometrically at 340 nm.

The antigens used in this example and the prior examples may be substituted with any one or more of the following anti-GHB (I or II), or any monoclonal or polyclonal antibodies of the same. All of these reactants can be used and will produce a detectable response in the presence of GHB.

EXAMPLE 10

The following procedure is a method for manufacturing a dry chemistry test strip, (DCD) for the determination of GHB in a test sample by measurement of its GHB concentration. Filter paper is impregnated with the following solutions and dried at 25 degree C.:

Solution 1

2-[N-Morpholino]ethanesulfonic Acid buffer (MES) 0.1 M anti-GHB is conjugated to horseradish peroxidase 900 mL D.I. water, mix, adjust pH to 6.0, and Q.S. to 1000 mL with D.I. water Solution 2

2-[N-Morpholino]ethanesulfonic Acid buffer 0.1 M

Tetramethylbenzidine, (TMB) 500 mg

Urea-Peroxide, 5.0 g 900 mL D.I. water, mix, and adjust pH between 5.0 and 7.0, preferably 6.0

Q.S. to 1000 mL with D.I. water lab note: the techniques for producing these types of conjugated antibodies is well known in the art.

This assay utilizes an antigen/antibody reaction with the antibody conjugated to peroxidase. When antibody which is conjugated to the peroxidase binds to its target antigen, it releases the peroxidase which is then free to react with peroxide and the chromogen, TMB, resulting in formation of a blue-green colored complex. This color reaction yields a visible color change. Therefore, the GHB concentration is proportional to the intensity of the blue-green color produced.

The test device in this example is manufactured in the same manner as that in Example 9. If this device is. constructed using two reaction pads, the reaction pad containing solution 2 must be on the bottom half of the "sandwich". In addition, it may be necessary to separate the two pads with a semipermeable membrane.

Changes to the foregoing solutions could be made and still have similar results. In addition, changes to the foregoing solution or use of the identical solutions could be utilized in an automated analyzer and produce the same results. The foregoing solutions could be combined together, or reduced to only 1. The concentrations of said constituents may also be changed and still remain within the scope of the invention. Obviously, the same substitution groups for anti-GHB are possible as already demonstrated in examples 1–9 and this includes the buffers as noted in the prior examples also apply to this example. The urea peroxide was chosen, because it is more stable than simple peroxide. It is obvious, however, that one may utilize any peroxide-containing compound to act as a substrate to peroxidase.

The TMB may be replaced by any suitable compound that will produce an observable color as part of the peroxidase/peroxide reaction. Other such compounds include ABTS (2,2'-Azino-di-(3-ethylbenzthiazolinesulfonic acid) diammonium salt, AEC (3-Amino-9-ethyl carbazole), 2-5, dimethyl-2,5-dihydroperoxyhexane, Bis{4-[N-(3'-sulfo-n-propyl)-N-n-ethyl]amino-2,6-dimethylphenyl}methane (Bis-MAPPS), N-Ethyl-N-(2-hydroxy-3-sulfopropyl)-3-methoxyaniline (ADOS), N-Ethyl-N-(3-sulfopropyl)-3-methoxyaniline (ADPS), N-Ethyl-N-(2-hydroxy-3-sulfopropyl)aniline (ALOS), N-Ethyl-N-(3-sulfopropyl)-3,5-dimethylaniline (MAPS), N-Ethyl-N-(2-hydroxy-3-sulfopropyl)-3-methylaniline (TOOS), N-Ethyl-N-(3-sulfopropyl)-3-methylaniline (TOPS), N-(3-sulfopropyl) aniline (HALPS), N-Ethyl-N-(2-hydroxy-3-sulfopropyl)-3,5-dimethoxy-aniline (DAOS), N-Ethyl-N-(3-sulfopropyl)-3,5-dimethoxyaniline (DAPS), N-Ethyl-N-(3-sulfopropyl) aniline (ALPS), N-(2-hydroxy-3-sulfopropyl)-3,5-dimethoxyaniline (HDAOS), N-(3-sulfopropyl)-3,5-dimethoxyaniline (HDAPS), N-Ethyl-N-(2-hydroxy-3-sulfopropyl)-3,5-dimethylaniline (MAO), N,N-Bis(4-sulfobutyl)-3,5-dimethylaniline (MADB), and pyrogallol. Also, 4-aminoantipyrine can be paired with a number of compounds to create a violet to violet-blue color complex in the presence of the peroxide/peroxidase reaction. These compounds include 2,4-Dichlorophenol, N,N-Diethyl-m-toluidine, p-Hydroxybenzene Sulfonate, N,N-Dimethylaniline, 3,5-Dichloro-2-Hydroxybenzenesulfonate, Sodium N-Ethyl-N-(3-Sulfopropyl)-m-Anisidine, and N-Ethyl-N-(2-hydroxy-3-Sulfopropyl)-m-toluidine. Another indicator pair that may be utilized consists of 3-Methyl-2-benzothiazolinonehydrazone and Dimethylaniline.

In addition, it is possible to conjugate other enzymes to antibodies or antigens. Consequently, these conjugated pairs can also be substituted into the test reaction together with an appropriate indicator compound. Therefore, this assay may include any enzyme capable of being conjugated to an antibody or antigen.

To further describe the preferred test method for determining the presence of GHB by the measurement in an unknown test sample, the assay system can take the form of a dipstick (DCD), lateral flow device (LFD), or an aqueous liquid reagent that is composed of a buffer and an indicator that produces a color or change in the intensity of color or absorbance in the UV or visible spectrum in the presence of GHB. The antibodies (such as anti-GHB, anti-anti-GHB, anti-IgG or others). The anti-GHB antibodies can also include IgA, IgD, IgE, and IgM. The buffers used may be any one or more compounds selected from the following group and enumerated by their common names: citrate, hepes, tris (trizma), taps, popso, tes, pipes, mopso, tricine, mops, mes, bicine, bes, caps, epps, dipso, ches, capso, ampso, aces, ada, bis-tris-propane, tapso, heppso, tea, amp, phosphate, phthalate, succinate, hydrochloric acid, sulfuric acid, nitric acid, acetic acid, sodium hydroxide, and potassium hydroxide. In addition, as taught the test sample can be any biological fluid from the following group: urine, serum, whole blood, saliva, cerebral spinal fluid, gastric contents, and extracts of hair or sweat. This art as taught herein can employ an aqueous-based liquid reagent for measuring the concentration of GHB, said test method comprising the steps of placing the reagent in the reagent compartment of the chemistry autoanalyzer, aliquoting samples, calibrators, and controls into sample cups and placing them on the chemistry autoanalyzer, transferring an aliquot of each sample, calibrator, and control into single, discrete cuvettes mounted within the chemistry autoanalyzer, aliquoting a specified volume of the reagent composition into each cuvette and mixing, incubating the reaction mixture for a specified time interval, measuring and recording absorbance values of the reaction mixtures with the chemistry autoanalyzer's spectrophotometer at the specified wavelength (from 340 to 800 mn) at preprogrammed time intervals, and comparing absorbance values of samples and controls to those of the calibrators in the form of a standard curve thereby quantitating the GHB if present.

This art as taught in previous examples can also employ a dry chemistry test strip (DCD) method for measuring the GHB concentration in a test sample, the method comprising the steps of preparing a test means by successively impregnating a carrier matrix with reagent solutions, drying said test means, dipping completed test means into test sample, and determining the quantity of GHB present in said test sample by comparing the relative intensity of the color produced by the reaction to a color chart with color blocks referenced to specific concentrations of GHB.

This art as taught in previous examples can also employ a dry chemistry, lateral flow device (LFD) for measuring the GHB concentration in a test sample, the method comprising the steps of preparing a test means by successively impregnating a solid, absorbent carrier matrix with liquid, reagent solutions at specific locations on the test means, drying said test means, dipping completed test means into test sample or pipetting test sample onto the test means, and determining the quantity of GHB in the test sample by comparing the relative intensity (completeness) of color developed to a standard chart.

EXAMPLE 11

The following procedure is a method for manufacturing a dry chemistry, lateral flow test strip for the determination of GHB. This example will also illustrate the utility of incorporating the use of creatinine concentration (as determined by calorimetric assay, DCD, LFD, antibody/antigen, etc. . . . ) on the same sample measured for GHB and the enhanced clinical significance of the GHB value. Absorbent material is successively impregnated with the following solutions and dried at 25 degree C.:

Solution I 0.05 M Phosphate buffer pH 7.2

30 fmol/L anti-GHB

Solution 2

0.05 M Phosphate pH 7.2

30 fmol/L 50 ug/mL of GHB bound to red microparticles

In this example, the lateral flow device is prepared in accordance with the instant invention. The lateral flow device is comprised of a paper carrier matrix impregnated with the compositions of solutions 1 and 2 as follows. Note that said concentrations of any of the above constituents can be varied to suit the lateral flow/dipstick device format (e.g. dependent upon paper type, and inclusion of semipermeable membranes or other innovations utilized in dry chemistry technology). Production of this test device is carried out using the following procedure. The test device made up of a solid support which includes an absorbent material capable of transporting a liquid by capillary action or wicking (e.g. nitrocellulose 5.0u, S&S brand) in this example having dimensions of 5 mm by 70 mm and can be backed by or in contact with strips of glass fiber (e.g. Whatman GF/A) to aid in controlling the wicking action. In this example, the device uses an GHB cutoff of 50 ug/mL.

The starting point or origin at which the sample is placed on the test device is 5 mm from one end of the strip, and 30 mm from this origin is the buffered solution 1 containing anti-GHB bound to the test strip 35 mm from the bottom edge of said test pad in a line approximately 1 mm wide by 5 mm long thereby extending from one side of the device to the other side forming the A, "assay line". A second buffered solution consisting of red colored particles bound (i.e. irreversibly coupled, conjugated, or covalently linked) to 50.0 ug/mL GHB is applied to the strip approximately 5 mm from the starting point (or 10 mm from the lower edge of the test strip) in a concentration as to make certain that assay line forms a solid visual line to achieve effective results.

A solid case made of plastic or other suitable material may be used to conceal and protect the device except for a assay line "window" (hole in the device for viewing the results of the analysis); and a window for sample application at the origin. This case may be composed of plastic, wood, cardboard, or other suitable material.

If the sample is positive, with a concentration of 50 ug/mL GHB or more the following occurs. A drop of urine (approximately 50 uL) is applied at the starting point or origin of the strip. The urine then migrates to the opposite or terminal end of the strip. The free GHB present (in a concentration of 50 ug/mL or greater of GHB) in the urine starts to migrate to the assay line and binds all of the bound anti-GHB at the assay line. The red particles bound with GHB will migrate with the urine toward the terminal end of the strip away from the starting point. These colored complexes will not bind to the line of anti-GHB bound at the 10 mm "A" line or assay window because all of the free GHB has already bound up all of the active sites of the bound (immobilized) anti-GHB at the assay line. The migrating red colored particle complexes, therefore, continue migrating up the device and disappear from view. Thus, no solid red line is formed indicating that a concentration of 50 ug/mL or more of GHB is present.

If the sample is negative, with a concentration of less than 50 ug/mL GHB present, the following occurs. The free (unbound) red GHB microparticles complexes migrate up to the "A" assay line and bind to the anti-GHB conjugated (immobilized) to the test strip at that location thereby forming a solid (complete) red line assay line. The formation of a solid red line indicates a negative for the presence of GHB in concentration of greater than 50 ug/mL.

The test strip can be placed on top of, or backed, with glass fiber (e.g. Whatman GF/A) in order to control (i.e. speed up,or slow down the "wicking" speed) and held in place by an adhesive or other means. This brief description of the present art illustrates a completely enabled device that would allow a physician, patient, and/or technician to determine rapidly the presence or absence of GHB in a urine or other suitable fluid.

If analysis is performed on a 24 hour urine collection, no further analysis is required. Proper 24 hour urine collections are difficult and inconvenient for the patient, however, the above test can also be performed using a random specimen. Consequently, a novel addition to further improve the ease of use and the accuracy of the present device requires an additional assay on the same random or spot urine used for the GHB assay. This additional assay is for creatinine, cystatin C or any other steady state marker consistently excreted in human urine. This analyte value can be used to "normalize" or correct the GHB test result for the amount of water present in the sample. Water content of a random urine sample is affected by the diurnal variations, diet, diuretics (e.g. caffeine, sugar, etc. . . . ) and short term fluid consumption (water consumed over the previous 2 to 3 hours). The amount of creatinine excreted by a normal, healthy individual is relatively consistent from day to day, and hour to hour; any GHB would also be excreted at a consistent rate from hour to hour. Creatinine or Cystatin C is, therefore, ideal for adjusting or normalizing the amount of GHB found in a random urine. Specifically, if for example the creatinine concentration is high the subject has consumed very little water over the previous few hours, and the GHB value will be elevated; if the subject has consumed a large volume of water just prior to testing, the creatinine value will be low and the GHB marker will also be depressed.

This present art incorporates the unique invention of the GHB analysis and determining the concentration of a steady state marker such as creatinine or Cystatin C ratio (GHB/creatinine). The following formula may be used to adjust the GHB value according to the creatinine concentration, and thereby produce the GHB/creatinine ratio (i.e. G/C ratio). This method requires division of the GHB value by the creatinine concentration of the sample. This yields a normalized GHB value for a random sample. The method of measuring creatinine in urine by LFD is hitherto unknown in the art until the present device and examples of this methodology will follow. If analysis is being performed via automated chemistry, a number of well known methods are currently available. This ratio provides the most convenient way to normalize the GHB value and allow the user, even an untrained one, to obtain a corrected GHB value.

The following is a detailed description of how the GHB/creatinine ratio is used. Obviously, in the case of testing the sample with aqueous, liquid reagents on an automated chemistry analyzer system quantitative results would be obtained for both analytes. The GHB value is then divided by the creatinine concentration. If this ratio is equal to, or greater than 0.27, then GHB presence is confirmed. Values lower than 0.27 are considered negative for GHB for this example.

In the example above, the device detects 50 ug/mL of GHB or more in the urine, so positives are considered 50, and negatives are zero. Typical creatinine values range from 45 to 180 mg/dl. Therefore, if the GHB result is positive and the creatinine value is less than 185 mg/dl, then the corrected result is still positive (50/185=0.27); the ratio is inversely proportional to the creatinine value (i.e. as the creatinine drops, the ratio increases). Obviously the higher the ratio, the more GHB present. Therefore, a semi-quantitative GHB/creatinine ratio can be obtained by assuming any positive is 50 ug/mL of GHB and dividing it by the creatinine quantitation (e.g. 50/60=0.833 ratio). On the other hand, if the creatinine concentration is higher than 185, then the true GHB value may be falsely elevated, and a new sample should be tested because this could be interpreted as a false positive.

Conversely, if the GHB value is negative, and the creatinine value is 157 mg/dl or higher, then.the sample is clearly negative (25 ug/mL/157 mg/dl=0.159). On the other hand if the creatinine value is lower than 20 mg/dl creatinine the assay should be repeated. It is well known in the art that a creatinine of less than 20 mg/dl is a dilute specimen and a false negative could occur with this specimen (25/20=1.25, a positive).

Another factor that can and should be taken into account is kidney function as determined by the protein/creatinine ratio. If the protein/creatinine ratio is normal (less than 3.0, as known in the art), then the assay is not affected by the ability of the kidneys to clear creatinine or other steady state marker such as cystatin C and allow for an accurate assessment of the urine concentration. If the protein/creatinine ratio is greater than 3.0, then the assay can be affected by the kidney function. The GHB/creatinine ratio may be corrected for kidney dysfunction by dividing it by the protein/creatinine ratio (i.e. GHB/K ratio), and determining appropriate ranges. Preliminary data suggests that an GHB/K ratio of 0.05 or higher is negative, and an GHB/K ratio of less than 0.05 indicates a positive for GHB.

To summarize Example 11 more specifically, the foregoing lateral flow/dry chemistry test strip (LFD) method for measuring the GHB concentration in a random urine sample, the method comprising the steps of preparing a test means by successively impregnating a solid, absorbent, carrier matrix with liquid reagent solutions at specific locations on said test means, drying said test means, dipping completed test means into test sample or pipetting sample onto the test means, and determining the quantity of GHB in said test sample by comparing the relative intensity (completeness) of the assay line produced by the reaction. Also, the assay. can include the determination of creatinine to determine the GHB/creatinine ratio (G/C ratio) to improve the validity of the test result. It is understood that the above example was purely illustrative, and that the relative positions of the control and assay lines could be relocated without changing the spirit, scope, or intent of the instant invention.

Changes to the foregoing solutions could be made and still have similar results. The foregoing solutions could be combined together, or reduced to include only 1 solution for impregnation. The concentrations of said constituents may also be changed and still remain within the scope of the invention. The antibody to GHB can be to can be replaced with antigens in appropriate positions to make for a different format than explained in the example. Anti-Anti-GHB could be used which is the antibody to the GHB antibody. The foregoing was merely illustrative of the possibilities of this novel and unique invention. In addition, anti-GBL could be used instead of anti-GHB and GBL could be conjugated to red-microparticles the assay would work for the detection of GBL in exactly the same manner as the GHB lateral flow method.

The buffer(s) used in example 11, may be substituted with any one or more of the buffers as illustrated in example 1.

The colored particles used in example 11 could be replaced with particles of any color, and made from many types of materials including rubber, latex, plastics, synthetic solids, metals, or other suitable material that will form a solid platform or substrate for the covalent attachment (binding) of a reactive compound, antibody, and/or antigen to it.

This Example's formulation could also include any one or more of the surfactants, thickeners, or interference-removing compounds disclosed above in this embodiment. Optional compounds for removal of interfering substances include mono, di, tri, and tetra sodium salts of EDTA or EGTA. Optional thickeners include polyvinylpyrrolidone, algin, carrageenin, casein, albumin, methyl cellulose, and gelatin in concentrations ranging from 0.5 to 5 g. per 100 ml. Optional surfactants may include long chain organic sulphates or sulphonates (e.g. Brij-35, Tween 20, Triton X-100, dioctyl sodium sulphosuccinate, and sodium lauryl sulphate).

The subject invention provides an extraordinary and novel method for quantitating the presence of GHB in biological specimen(s) (i.e. urine, blood, serunm, saliva, hair and sweat extracts, and cerebrospinal fluid) and other fluids such as water, beverages (to include but not be limited to soft drinks, beer, mixed drinks, etc.) in order to determine the presence of GHB.

In addition, the absolute novelty of creatinine, cystatin C, or other renal clearance marker measurement by the use of a DCD or LFD is of enormous value to medical diagnostics, enforcement agencies, and public safety and health organizations; its utility when applied to aqueous, liquid form and modified for use on automated clinical chemistry analyzers is also of great value for the same reasons. All in all, the ability of the present art to analyze urine for GHB measurement via dry chemistry dipsticks, lateral flow devices, and aqueous, liquid reagents while simultaneously enabling the user to normalize the results-with the sample's creatinine, cystatin C or other renal clearance marker concentration as described herein is a substantial and significant improvement over the prior art.

To further elaborate the present art so that it is clearly understood the present art is a method for determining the presence of GHB on an unknown test sample, said test method being composed of a buffer and indicator that produces a detectable response or a change in the absorbance or intensity of a color or line in the UV or visible spectrum in the presence or absence of GHB. These methods can use all the buffers, indicators, microparticles (metallic or other matrix), and components as taught in examples 1 through 11. The methods in examples 1 through 11 as taught can be employed as aqueous liquid reagents for measuring the concentration of GHB on a test specimen, said test methods comprise the steps of placing the reagent in the reagent compartment of the chemistry autoanalyzer and aliquoting samples, calibrators, and controls into sample cups and placing them on the chemistry autoanalyzer, then transferring an aliquot of each sample, calibrator, and control into single, discrete cuvettes mounted within the chemistry autoanalyzer, aliquoting a specified volume of the reagent composition into each cuvette and mixing, incubating the reaction mixture for a specified time interval, and measuring and recording absorbance values of the reaction mixtures with the chemistry autoanalyzer's spectrophotometer at the specified wavelength (from 340 to 800 nm) at preprogrammed time intervals, and comparing absorbance values of samples and controls to those of the calibrators in the form of a standard curve thereby quantitating the amount of GHB present. The methods as taught can also employ a dry chemistry test strip (DCD) method to measure the GHB concentration in a test sample, the method comprising the steps of preparing a test means by successively impregnating an absorbent carrier matrix with reagent solutions, drying said test means, dipping completed test means into test sample, and determining the quantity of GHB present in said test sample by comparing the relative intensity of the color produced by the reaction to a color chart with color blocks referenced to specific concentrations of GHB. The methods as taught can also be used for any general chemistry "test pad" or pads that are currently used or will be used in the art like in the DCD device a further integration in a device such as the DLFH, in this advance technology, the manufacturing process includes impregnating onto an absorbent, solid carrier (e.g. paper) called in this example, the "test pad", in exactly the same manner as with the DCD's with similar constituents. The test pad, once impregnated, is dried, then mounted onto a solid support (nitrocellulose membrane) that is capable of transporting (through lateral flow) liquid to the test pad from the point of application of a test sample. In simpler terms, the device is dipped into a liquid or the liquid sample is placed on the device at the bottom or starting point for the assay. The liquid migrates from the starting application point to the opposite end of the nitrocellulose lateral flow paper, during which the test pad becomes saturated with the sample. The reaction takes place on the test pad and color develops. The developed color is then compared to a color chart with known concentrations of GHB that has the appropriate colors relative to each specific concentration of GHB. The results are then recorded. Note, the test pad must be an absorbent (wicking) material that permits migration of sample up the solid absorbent test pad and allows analytes and reactants to interact. In this example the inventor illustrates the ability of the present device to use any GHB reaction indicator that will produce a detectable response in the presence of GHB.

The methods can also employ a dry chemistry lateral flow device (LFD) for measuring the GHB concentration in a test sample, the method comprising the steps of preparing a test means by successively impregnating a solid, absorbent carrier matrix with liquid reagent solutions at specific locations on said test means, drying said test means, dipping completed test means into test sample or pipetting test sample onto the test means, and determining the quantity of GHB present in said test sample by comparing the relative intensity of the assay line produced by the reaction to a standard chart, or by comparing the relative intensity of the assay line produced by the reaction to the control line. The method examples as taught utilizing a spectrophotometer can employ wavelengths from 340 to 800 nm.

The methods as the present art teaches can also improve analytical value of the GHB concentration of a test sample by employing creatinine, cystatin C, or specific gravity concentrations which can be used to normalize the sample for accurate determination of GHB. This normalization of the GHB concentration requires that it be divided by the creatinine, cystatin C, or specific gravity concentration of the same test sample thereby yielding the GHB to creatinine, cystatin C, or specific gravity ratio. Thus, all the methods of the present art as taught are for analyzing a sample using a dry chemistry dipstick, dipstick/lateral flow hybrid, lateral flow device, or aqueous liquid reagent to determine the concentration of GHB in an individual's random urine sample in order to determine if the individual's has ingested GHB, and normalizing or correcting this assay value with the sample's creatinine, cystatin C, or specific gravity concentration.

Changes to the above reagent solution of example 11 can be made and still remain within the scope and function of this invention and will have similar results to examples 1 through 10 above. The indicator(s) and buffer(s) of example 11 can be replaced by all the examples and possible substitutions as illustrated in examples 1 through 10. It can be noted that in any of the previous examples that the reagent solutions 1 and 2 can be combined to form one reagent solution and still be functional.

Changes to the above compound(s) used in the example(s) can be exchanged with analogs or functional derivatives of the compound(s) and still within the scope of the appended claims.

This brief description of the present art illustrates a completely enabled device that would allow a physician, patient, individual, enforcement agency, bar tender, parent, and/or technician to quickly and easily determine the presence of GHB or GBL in urine, providing a much needed advancement in the art of drug testing.

To briefly explain the present device as taught. The present art includes a device for the detection of GHB in a sample of urine submitted for drugs testing the steps comprise of preparing a dry chemistry test means by successively impregnating a solid, carrier matrix with reagent solutions containing an indicator and a buffer, and drying the impregnated, solid carrier matrix. Finally, by dipping said dry chemistry test means into urine, one can observe the detectable response in the form of a color developed in the presence or absence of GHB. This present art also illustrates a unique device that will prevent cross contamination (runover) of test pads on the same dipstick, as well as a unique dry chemistry test pad lateral flow device hybrid. These methods can incorporate detectable responses in the visible color range to the human eye or in the visible light spectrum. These methods have a wide sample choice other than urine, and can be replaced by any biological sample including serum, whole blood, cerebral spinal fluid, gastric fluid, hair homogenates, sweat extracts, saliva or other biological fluid and other fluid to include water, soft drinks, beverages, beer, mixed drinks, drinks with alcohol, etc.

As completely described and enabled the methods for determining the presence or amount of gamma-hydroxybutyrate (GHB) or gamma-butyrolactone in a sample, said methods comprising contacting said sample with an indicator which specifically binds to GHB or GBL to form an indicatorcomplex; and, measuring said indicatorcomplex to determine the presence or amount of said GHB or GBL in said sample.

The type of sample for the methods of examples 1 through 11 can be selected from the following group consisting of urine, serum, whole blood, cerebral spinal fluid, gastric fluid, hair homogenates, sweat extracts, saliva, water, beverages, beer, alcoholic drinks, or soft drinks.

To further delineate the foregoing teachings the methods for the detection of GHB or GBL in a sample can also comprise the steps of preparing a dry chemistry test means by successively impregnating a solid, carrier matrix with reagent solutions containing an indicator and a buffer, and drying the impregnated,; solid carrier matrix, and finally placing sample onto said dry chemistry test means, and observing the detectable response in the form of a color developed in the presence or absence of GHB or GBL.

And the methods as completely taught for the detection of GHB in a sample can comprise the steps of placing aliquots of an unknown urine and calibrator to be tested in automated analyzer sampling cups, placing the cups in a sampling tray within an automated analyzer, transferring the aliquots of sample and calibrator to cuvettes mounted within the automated analyzer, injecting a first reagent composition (R-1) comprising an indicator and buffer in an aqueous medium into the cuvettes, mixing sample and reagent, reading the absorbance values of reaction mixture composed of reagents and test samples (said test samples include unknown specimens, controls, and calibrator) at specified intervals, in accordance with a preprogrammed code introduced into the automated analyzer, at a preprogrammed monochromatically specified wavelength, and comparing absorbance of the first reagent composition plus the unknown samples with that of the first reagent composition plus the calibrator containing a zero reference point, and thereby determining the presence or absence of GHB.

It is understood that variations or modifications in the following embodiments may be made by someone skilled in the art without departing from the spirit and scope of the invention. All such modifications and variations are to be included within the scope of the invention as defined in the appended claims:

I claim:

1. A method for quantitatively determining gamma hydroxybutyrate comprising: contacting a sample with the mixture of an esterase, a pH indicator dye and a buffer; determining a color change in the mixture and correlating a color change with the amount of GHB in the sample.

2. The method according to claim 1 wherein the esterase is hydroxybutyrate dehydrogenase or carboxyl esterase.

3. The method according to claim 1 wherein the pH indicator is selected from the group consisting of thymol blue, bromcresol green, methyl red, cresol red, metanil yellow, m-cresol purple, xylenol blue, thymol blue, tropeolin OO, quinaldine red, α-dinitrophenol, methyl yellow; dimethyl yellow, bromophenol blue, tetrabromophenol blue, bromochlorophenol blue, Congo red, methyl orange, p-ethoxychrysoidine hydrochloride, napthyl red, alizarin sodium sulfonate, bromocresol green, γ-dinitrophenol, methyl red, lacmoid, chlorophenol red, benzoyl auramine G, bromocresol purple, bromophenol red, p-nitrophenol, bromthymol blue, phenol red, p-quinonemono(bis-4-oxyphenylmethide), neutral red, quinoline blue, α-naphtholphthalein, tropeolin OOO; α-napthol orange, ethyl bis(2,4-dinitrophenyl)acetate, di-o-cresolphthalide, phenolphthalein, thymolphthalein, dimethyl-phenolphthalein, alizarin yellow GG; salicyl yellow, alizarin yellow R, Nile blue, 2,4,6-trinitrophenylmethyl-nitramine, tropeolin O, triphenylrosaniline sulfonic acid (sodium or potassium salt), indigo carmine, nitrobenzene, bromcresol green, bromcresol purple, bromchlorophenol blue, brilliant yellow, brilliant blue R, brilliant cresyl blue ALD, brilliant blue G, briliant black BN, bromthymol blue, bromphenol red, bromphenol red, bromoxylenol blue, coomasie blue, azolitmin, litmus, pyrogallosulfonphthalein, and pyrogallo red-molybdate.

4. The method according to claim 1 wherein the buffer is selected from the group consisting of Hepes, citrate, borate, borax, sodium tetraborate decahydrate, sodium perchlorate, sodium chlorate, sodium carbonate, TRIS (Tris [hydroxymethyl]aminomethane, MES (2-[N-Morpholino] ethanesulfonic acid), BIS-TRIS (bis[2-Hydroxyethyl] iminotris[hydroxymethyl]methane; 2-bis[2-hydroxyethyl] amino-2-[hydroxymethyl-1,3-propanediol), ADA (N-[2-Acetamidol]-2-iminodiacetic acid; N-[Carbaoylmethyl] iminodiacetc acid), ACES (2-[(2-Amino-2-oxoethyl)amino] ethanesulfonic acid; N-[2-Acetamido]-2-aminoethanesulfonic acid), PIPES (PiperazineN-N'-bis[2-ethanesulfonic acid)]; 1,4-Piperzinedethanesulfoic acid), MOPSO (3-[N-Morpholinol]-2-hydroxypropanesulfonic acid), BIS-TRIS PROPANE (1,3-bis[tris(Hydroxymethyl) methylamino]propane), BES (N,N-bis[2-Hydroxyethyl]-2-aminoethaesulfonic acid; 2-bis(2-Hydroxyethyl)amino] ethanesulfonic acid), MOPS (3-[N-Morpholino] propanesulfonic acid), TES (N-tris[Hydroxymethyl]methyl-2-aminomethanesulfonic acid; 2[2-Hysroxy-1,1-bis (hydroxymethyl)-ethyl]amino)ethanesulfonic acid), DIPSO (3-[N,N-bis(2-Hydroxyethyl)amino]-2-hydroxypropane-sulfonic acid), TAPSO (3-[N-tris(Hydroxyethyl) methylamino]-2-hydroxypropanesulfonic acid), HEPPSO (N-[2-Hydroxythyl]piperazine-N'-[2Hydroxypropane-sulfonic acid]), POPSO (Piperazine-N,N'-bis[2-hydroxypropanesulfonic acid]), EPPS (N-[2-Hydroxyethyl] piperazine-N'-[3-propanesulfonic acid), TEA (triethanolamine), TRICINE (N-tris[Hydroxymethyl] methyllycine; N-[2-Hydroxy-1-1-bis(hydroxymethyl)etyyl] glycine), BICINE (N,N-bis[2-Hydroxyethyl]glycine), TAPS (N-tris[Hydroxymethyl]methyl-3-aminopropanesulfonic acid; ([2-Hdroxy-1,1-bis(hydroxymethyl)ethyl]amino)-1-propanesulfonic acid), AMPSO (3-[(1,1-Dimethyl-2-hydroxyethyl)amino]-2-hydroxypropanesulfonic acid), CHES (2-[N-Cyclohexylamino]ethanesulfonic acid), CAPSO (3-[Cyclohexylamino]-2-hydroxy-1-propanesulfonic acid), AMP 2-Amino-2-ethyl-1-propanol, CAPS (3-[cyclohexylamino]-1-propanesulfonic acid), hydrochloric acid, phosphoric acid, lactic acid, sulfiuric acid, nitric acid, chromic acid, boric acid, perchloric acid, potassium hydrogen tartrate, potassium hydrogen phthalate, calcium hydroxide, phosphate, bicarbonate, sodium hydroxide, potassium hydroxide, oxalate and succinate.

5. A method for quantitatively determining gamma hydroxybutyrate comprising: contacting a sample with the mixture of an enzyme conjugated to GHB-antibody, enzyme substrate, and a buffer; determining a color change in the mixture; and correlating the color change in the mixture with the amount of GHB in the sample.

6. The method according to claim 5 wherein the enzyme is selected from the group consisting of glycosidases, esterases, sulfatases, phosphatases, hydroxylases and oxidoreductases.

7. The method according to claim 5 wherein the buffer is selected from the group consisting of Hepes, citrate, borate, borax, sodium tetraborate decahydrate, sodium perchlorate, sodium chlorate, sodium carbonate, TRIS (Tris [hydroxymethyl]aminomethane, MES (2-[N-Morpholino] ethanesulfonic acid), BIS-TRIS (bis[2-Hydroxyethyl] iminotris[hydroxymethyl]methane; 2-bis[2-hydroxyethyl] aamino-2-[hydroxymethyl-1,3-propanediol), ADA (N-[2-Acetamidol]-2-iminodiacetic acid; N-[Carbaoylmethyl] iminodiacetc acid), ACES (2-[(2-Amino-2-oxoethyl)amino] ethanesulfonic acid; N-[2-Acetamido]-2-aminoethanesulfonic acid), PIPES (PiperazineN-N'-bis[2-ethanesulfonic acid)]; 1,4-Piperzinedethanesulfoic acid), MOPSO (3-[N-Morpholinol]-2-hydroxypropanesulfonic acid), BIS-TRIS PROPANE (1,3-bis[tris(Hydroxymethyl) methylamino]propane), BES (N,N-bis[2-Hydroxyethy]-2-aminoethaesulfonic acid; 2-bis(2-Hydroxyethyl)amino] ethanesulfonic acid), MOPS (3-[N-Morpholino] propanesulfonic acid), TES (N-tris[Hydroxymethyl]methyl-2-aminomethanesulfonic acid; 2[2-Hysroxy-1,1-bis (hydroxymethyl)-ethyl]amino)ethanesulfonic acid), DIPSO (3-[N,N-bis(2-Hydroxyethyl)amino]-2-hydroxypropane-sulfonic acid), TAPSO (3-[N-tris(Hydroxyethyl)

methylamino]-2-hydroxypropanesulfonic acid), HEPPSO (N-[2-Hydroxythyl]piperazine-N'-[2Hydroxypropanesulfonic acid]), POPSO (Piperazine-N,N'-bis[2-hydroxypropanesulfonic acid]), EPPS (N-[2-Hydroxyethyl]piperazine-N'-[3-propanesulfonic acid), TEA (triethanolamine), TRICINE (N-tris[Hydroxyethyl]methyllycine; N-[2-Hydroxy-1-1-bis(hydroxymethyl)etyyl]glycine), BICINE (N,N-bis[2-Hydroxyethyl]glycine), TAPS (N-tris[Hydroxymethyl]methyl-3-aminopropanesulfonic acid; ([2-Hdroxy-1,1-bis(hydroxyrnethyl)ethyl]amino)-1-propanesulfonic acid), AMPSO (3-[(1,1-Dimethyl-2-hydroxyethyl)amino]-2-hydroxypropanesulfonic acid), CHES (2-[N-Cyclohexylamino]ethanesulfonic acid), CAPSO (3-[Cyclohexylamino]-2-hydroxy-1-propanesulfonic acid), AMP 2-Amino-2-ethyl-1-propanol, CAPS (3-[cyclohexylamino]-1-propanesulfonic acid), hydrochloric acid, phosphoric acid, lactic acid, sulfuric acid, nitric acid, chromic acid, boric acid, perchloric acid, potassium hydrogen tartrate, potassium hydrogen phthalate, calcium hydroxide, phosphate, bicarbonate, sodium hydroxide, potassium hydroxide, oxalate and succinate.

* * * * *